(12) United States Patent
Amirouche

(10) Patent No.: US 9,248,030 B2
(45) Date of Patent: Feb. 2, 2016

(54) DEVICE AND METHOD OF SPACER AND TRIAL DESIGN DURING JOINT ARTHROPLASTY

(71) Applicant: Farid Amirouche, Highland Park, IL (US)

(72) Inventor: Farid Amirouche, Highland Park, IL (US)

(73) Assignee: Orthos Sensing Technologies, Chicago, IL (US)

( * ) Notice: Subject to any disclaimer, the term of this patent is extended or adjusted under 35 U.S.C. 154(b) by 0 days.

(21) Appl. No.: 14/186,963

(22) Filed: Feb. 21, 2014

(65) Prior Publication Data

US 2014/0243840 A1    Aug. 28, 2014

Related U.S. Application Data

(63) Continuation of application No. 13/406,159, filed on Feb. 27, 2012, now Pat. No. 8,656,790, which is a continuation of application No. 11/393,098, filed on Mar. 29, 2006, now Pat. No. 8,141,437.

(51) Int. Cl.
| | |
|---|---|
| *G01D 7/00* | (2006.01) |
| *G01L 1/22* | (2006.01) |
| *A61F 2/46* | (2006.01) |
| *A61F 2/38* | (2006.01) |

(Continued)

(52) U.S. Cl.
CPC ............... *A61F 2/4657* (2013.01); *A61F 2/389* (2013.01); *G01L 1/2225* (2013.01); *G01L 5/0019* (2013.01); *A61F 2/4684* (2013.01); *A61F 2002/30668* (2013.01); *A61F 2002/4666* (2013.01)

(58) Field of Classification Search
USPC ............................................................ 73/781
See application file for complete search history.

(56) References Cited

U.S. PATENT DOCUMENTS

| | | |
|---|---|---|
| 3,826,145 A | 7/1974 | McFarland |
| 4,094,192 A | 6/1978 | Watson et al. |
| 4,501,266 A | 2/1985 | McDaniel |

(Continued)

FOREIGN PATENT DOCUMENTS

| | | |
|---|---|---|
| DE | 197 09 960 A | 9/1998 |
| DE | 200 16 635 U | 2/2001 |

(Continued)

OTHER PUBLICATIONS

Beard, B.J., Natarajan, R.N., Andriacchi, T.P., Amirouche, F.M.L., "The Stress Origins of a New Striated Wear Pattern in a Total Knee Replacements," 42nd Annual Meeting of Orthopedic Research Society, (Feb. 1996) pp. 465.

(Continued)

*Primary Examiner* — Lisa Caputo
*Assistant Examiner* — Jamel Williams
(74) *Attorney, Agent, or Firm* — Brinks Gilson & Lione

(57) ABSTRACT

A spacer block for gathering data to be used in the balancing of the joint arthroplasty or repair and in the selection of a trial insert which includes a first body piece and a second body piece. A plurality of sensors and a processor are positioned between the first body piece and the second body piece when the pieces are assembled together to form the spacer block. A chim is removably mounted to a top surface of the second body piece, the chim is associated with the plurality of sensors and positioned in relation to the plurality of sensors such that a force exerted on the chim by a weight bearing surface is detected by the plurality of sensors.

18 Claims, 38 Drawing Sheets

(51) Int. Cl.
*G01L 5/00* (2006.01)
*A61F 2/30* (2006.01)

(56) References Cited

U.S. PATENT DOCUMENTS

| | | | |
|---|---|---|---|
| 4,573,362 | A | 3/1986 | Amlani |
| 5,197,488 | A | 3/1993 | Kovacevic |
| 5,360,016 | A * | 11/1994 | Kovacevic ............... 600/595 |
| 5,470,354 | A | 11/1995 | Hershberger et al. |
| 5,489,311 | A | 2/1996 | Cipolletti |
| 5,533,519 | A | 7/1996 | Radke et al. |
| 5,656,785 | A | 8/1997 | Trainor |
| 5,733,292 | A * | 3/1998 | Gustilo et al. ............... 606/88 |
| 5,813,406 | A | 9/1998 | Kramer et al. |
| 5,850,044 | A | 12/1998 | Spletzer |
| 5,880,976 | A | 3/1999 | Digioia, III |
| 6,213,958 | B1 | 4/2001 | Winder |
| 6,245,109 | B1 | 6/2001 | Mendes et al. |
| 6,354,155 | B1 * | 3/2002 | Berme ............... 73/862.043 |
| 6,362,768 | B1 | 3/2002 | Younis et al. |
| 6,385,475 | B1 | 5/2002 | Cinquin et al. |
| 6,447,448 | B1 | 9/2002 | Ishikawa et al. |
| 6,758,850 | B2 | 7/2004 | Smith et al. |
| 6,821,299 | B2 | 11/2004 | Kirking et al. |
| 7,097,662 | B2 | 8/2006 | Evans, III et al. |
| 7,179,295 | B2 | 2/2007 | Kovacevic |
| 7,188,535 | B1 | 3/2007 | Spletzer |
| 7,195,645 | B2 | 3/2007 | Disilvestro et al. |
| 7,381,223 | B2 | 6/2008 | Kovacevic |
| 7,470,288 | B2 | 12/2008 | Dietz et al. |
| 8,141,437 | B2 * | 3/2012 | Amirouche et al. ..... 73/862.041 |
| 2004/0019382 | A1 | 1/2004 | Amirouche et al. |
| 2004/0064073 | A1 | 4/2004 | Heldreth |
| 2004/0254771 | A1 | 12/2004 | Riener et al. |
| 2005/0049603 | A1 | 3/2005 | Calton et al. |
| 2005/0113932 | A1 | 5/2005 | Kovacevic |
| 2005/0267485 | A1 | 12/2005 | Cordes et al. |
| 2006/0009856 | A1 | 1/2006 | Sherman et al. |
| 2006/0062442 | A1 | 3/2006 | Arnaud et al. |
| 2008/0306413 | A1 | 12/2008 | Crottet et al. |
| 2009/0005876 | A1 | 1/2009 | Dietz et al. |

FOREIGN PATENT DOCUMENTS

| | | |
|---|---|---|
| EP | 0 979 636 A | 2/2002 |
| WO | WO 92 17113 A | 10/1992 |
| WO | WO 97 30652 A | 8/1997 |
| WO | WO 99 35972 A | 7/1999 |
| WO | WO 01 15058 A | 3/2001 |
| WO | WO 2005/122968 A2 | 12/2005 |

OTHER PUBLICATIONS

Natarajan, R.N., Andriacchi, T.P. Beard, B.J., Amirouche, F.M.L., "Fatigue Failure Prediction in the Polyethylene Component of a Total Knee Replacement Based on Cyclic Rolling," BED-vol. 33, Bioengineering Conference, ASME, (1996) pp. 421-422.

Giachetti, R.S., Amirouche, F.M., Aram, L.A., Gonzalez, M., "Biomechanical Problems with Contact Pressure Distribution in the Knee Joint After Total Knee Arthroplasty," Advances in Bioengineering, BED-vol. 48, ASME (2000) pp. 135-136.

Amirouche, F., Aram, L., Gonzalez, M., Giachetti, R., Mahr, C., "The Fitting of the Human Joint Through Micro Implanted Sensors", 1st Annual International IEEE-EMBS Special Topic Conference on Microtechnologies in Medicine & Biology, (Oct. 2000) pp. 518-520.

Aram, L., Amirouche, F., Gonzalez, M., Giachetti, R., "Characterization of Contact Pressure in Total Knee Arthroplasty as a Function of Component Position and Ligament Balance," International Society of Biomechanics XV111th Congress, http://congress.akm.ch/abstract/abstract/abt.abs_ausgabe?xssprache=ENG&xsdesign=OPT accessed on (Mar. 2003) 2-pgs.

Amirouche, F., Giachetti, R., Aram, L., Gonzalez, M., "Validation of a Finite Element Contact Model for the Use in Total Knee Arthroplasty," International Society of Biomechanics XVIIIth Congress, http://congress.akm.ch/abstract/abstract/abt.abs_ausgabe?xssprache=ENG&xsdesign=OPT. accessed on (Mar. 2003) 2-pgs.

Varadarajan, R., Amirouche, F., Wagner, F., Guppy, K., "A Finite Element Study of Osteoporosis in a Disc Degenerated Lumbar Spine Subject to Axial Compression," Proceedings of IMECE2002 ASME International Mechanical Engineering Congress & Exposition (Nov. 2002) pp. 381-382.

Amirouche, F., Gonzalez, M., Aram, L., "A Contact Pressure Based Prosthetic Fitting Device for a Total Knee Arthroplasty (TKA)" pp. 1-9.

Durkin M. C., Aram, L., Amirouce, F., Gonzalez, M. H., "Sensitivity and Error Analysis in Conjunction with Tibial Intramedullary Guides in Total Knee Arthroplasty," Journal of Prosthetics and Orthotics vol. 13, No. 2, p. 54. http://www.oandp.org/jpo/library/2001_02_054.asp, accessed on (Jun. 2003) pp. 1-10.

Novotny, J., Gonzalez, M.H., Amirouche, F.M.L., Li, Y.C., "Geometrical Analysis of Potential Error in Using Femoral Intramedullary Guides in Total Knee Arthroplasty," The Journal of Arthroplasty vol. 16, No. 5 (2001) pp. 641-647.

Chandran, N., Amirouche, F., Goldstein, W., Barmada, R., "Effect of Malalignment and Friction on Contact Pressure in the Polyethylene Component in the Total Knee Replacement," Proceedings of IMECE2002 ASME International Mechanical Engineering Congress & Exposition (Nov. 2002) pp. 423-424.

Amirouche, F., Aram, L., Gonzalez, M., Giachetti, R., Mahr, C., "The Fitting of the Human Joint Through Micro Implanted Sensors," 1st Annual International IEEE-EMBS Special Topic Conference on Microtechnologies in Medicine & Biology, (Oct. 2000) pp. 518-520.

Amirouche, F., Giachettie, R., Aram, L., Gonzalez, M., "Induced Stress in TKA Resulting from Malrotation," Bioengineering Conference, BED-V 1.50, ASME (2001) pp. 245-246).

Chandran, N., Amirouche, F., Gonzalez, M., Barmada, R., "Effect of Slope Changes in Posterior Stabilizer on the Rollback Mechanism of the Knee in Flexion-Extension," Bioengineering Conference (Jun. 2003) 2-pgs.

Lopez, C.G., Amirouche, F., Wagner, F.C., Guppy, K.H., "Development and Validation of a Three-Dimensional Parametric Model of the Cervical Spine," Proceedings of IMECE2002, ASME International Mechanical Engineering Congress & Exposition, (Nov. 2002) pp. 383-384.

Yi-Chun, Li, Y., Lavender, S.A., Natarajan, R.N., Andersson, G.B.J., Amirouche, F.M.L., "Kinematic and Kinetic Analyses in Full-Body Asymmetric Lifting," Advances in Bioengineering, BED-vol. 1, 43 (1999) pp. 187-188).

"A Patient's Guide to Artificial Knee Replacement," MMG—Patient Education TOC, http://www.medicalmultimediagroup.com/pated/joints/knee/knee_replacement.html, accessed on (Mar. 2003) pp. 1-7.

International Search Report, dated Dec. 8, 2003 of Application No. PCT/US03/08591.

* cited by examiner (TOP) Dimensions That Change According To Size

| | d6 | d56 | d53 | d3 | d2 | d4 | d151 | d150 |
|---|---|---|---|---|---|---|---|---|
| SIZE_1P5_TH10 | 0.390 | 2.394 | 1.600 | 1.730 | 0.380 | 0.820 | 0.396 | 0.660 |
| SIZE_3_TH10 | 0.500 | 2.800 | 1.850 | 2.000 | 0.560 | 0.900 | 0.314 | 1.150 |
| SIZE_6_TH10 | 0.650 | 3.504 | 2.323 | 2.400 | 0.750 | 1.178 | 0.503 | 1.680 |
| SIZE_4_TH10 | 0.560 | 3.051 | 2.012 | 2.154 | 0.649 | 0.975 | 0.324 | 1.394 |

| | d149 | d136 | d139 | d241 | d460 | d240 | d376 | d365 |
|---|---|---|---|---|---|---|---|---|
| SIZE_1P5_TH10 | 0.760 | 1.525 | 1.020 | 0.112 | 0.608 | 1.280 | 1.730 | 0.645 |
| SIZE_3_TH10 | 1.270 | 1.760 | 1.200 | 0.130 | 0.703 | 1.520 | 2.000 | 0.725 |
| SIZE_6_TH10 | 1.750 | 2.095 | 1.400 | 0.163 | 0.883 | 1.830 | 2.400 | 1.003 |
| SIZE_4_TH10 | 1.510 | 1.892 | 1.289 | 0.142 | 0.765 | 1.649 | 2.154 | 0.800 |

| | d312 | d276 | d375 | d477 | d498 | d495 | d494 | d462 |
|---|---|---|---|---|---|---|---|---|
| SIZE_1P5_TH10 | 0.325 | 0.080 | 0.130 | 0.560 | 0.927 | 0.900 | 0.250 | 0.830 |
| SIZE_3_TH10 | 0.388 | 0.080 | 0.150 | 0.675 | 1.110 | 0.900 | 0.250 | 1.100 |
| SIZE_6_TH10 | 0.575 | 0.090 | 0.077 | 0.825 | 1.422 | 0.988 | 0.250 | 1.378 |
| SIZE_4_TH10 | 0.441 | 0.081 | 0.142 | 0.737 | 1.222 | 0.916 | 0.250 | 1.192 |

| | d461 | d530 | d529 | d581 |
|---|---|---|---|---|
| SIZE_1P5_TH10 | 0.420 | 0.420 | 0.470 | 1.000 |
| SIZE_3_TH10 | 0.420 | 0.420 | 0.470 | 1.220 |
| SIZE_6_TH10 | 0.420 | 0.420 | 0.748 | 1.500 |
| SIZE_4_TH10 | 0.420 | 0.420 | 0.562 | 1.300 |

Figure 13a (TOP) Dimensions That Change According To Thickness

| | d0 | d464 | d531 |
|---|---|---|---|
| SIZE_6_TH8 | 0.501 | 0.108 | 0.108 |
| SIZE_6_TH10 | 0.580 | 0.177 | 0.177 |
| SIZE_6_TH12P5 | 0.659 | 0.256 | 0.256 |
| SIZE_6_TH15 | 0.747 | 0.344 | 0.344 |
| SIZE_6_TH17P5 | 0.845 | 0.442 | 0.442 |
| SIZE_6_TH20 | 0.943 | 0.540 | 0.540 |
| SIZE_1P5_TH8 | 0.480 | 0.108 | 0.108 |
| SIZE_1P5_TH10 | 0.559 | 0.177 | 0.177 |
| SIZE_1P5_TH12P5 | 0.638 | 0.256 | 0.256 |
| SIZE_1P5_TH15 | 0.726 | 0.344 | 0.344 |
| SIZE_1P5_TH17P5 | 0.824 | 0.442 | 0.442 |
| SIZE_1P5_TH20 | 0.922 | 0.540 | 0.540 |
| SIZE_3_TH8 | 0.480 | 0.108 | 0.108 |
| SIZE_3_TH10 | 0.559 | 0.177 | 0.177 |
| SIZE_3_TH12P5 | 0.638 | 0.256 | 0.256 |
| SIZE_3_TH15 | 0.726 | 0.344 | 0.344 |
| SIZE_3_TH17P5 | 0.824 | 0.442 | 0.442 |
| SIZE_3_TH20 | 0.922 | 0.540 | 0.540 |
| SIZE_4_TH10 | 0.564 | 0.177 | 0.177 |
| SIZE_4_TH12P5 | 0.643 | 0.256 | 0.256 |

Figure 13b (BOTTOM) Dimensions That Change According To Size

| | d6 | d56 | d53 | d513 | d2 | d4 | d151 | d150 |
|---|---|---|---|---|---|---|---|---|
| SIZE_1P5_TH10 | 0.390 | 2.394 | 1.600 | 0.080 | 0.380 | 0.820 | 0.396 | 0.680 |
| SIZE_3_TH10 | 0.500 | 2.800 | 1.850 | 0.080 | 0.560 | 0.900 | 0.314 | 1.150 |
| SIZE_6_TH10 | 0.650 | 3.504 | 2.323 | 0.090 | 0.750 | 1.178 | 0.503 | 1.680 |
| SIZE_4_TH10 | 0.560 | 3.051 | 2.012 | 0.081 | 0.649 | 0.975 | 0.324 | 1.394 |

| | d149 | d136 | d139 | d241 | d460 | d240 | d380 | d365 |
|---|---|---|---|---|---|---|---|---|
| SIZE_1P5_TH10 | 0.760 | 1.525 | 1.020 | 0.112 | 0.608 | 1.280 | 2.144 | 0.695 |
| SIZE_3_TH10 | 1.270 | 1.760 | 1.200 | 0.130 | 0.703 | 1.520 | 2.550 | 0.775 |
| SIZE_6_TH10 | 1.750 | 2.095 | 1.400 | 0.163 | 0.883 | 1.830 | 3.254 | 1.053 |
| SIZE_4_TH10 | 1.510 | 1.892 | 1.289 | 0.142 | 0.765 | 1.649 | 2.801 | 0.850 |

| | d312 | d276 | d3 | d376 | d537 | d514 | d630 | d562 |
|---|---|---|---|---|---|---|---|---|
| SIZE_1P5_TH10 | 0.375 | 0.130 | 1.730 | 1.730 | 1.730 | 0.645 | 0.470 | 0.325 |
| SIZE_3_TH10 | 0.438 | 0.130 | 2.000 | 2.000 | 2.000 | 0.725 | 0.470 | 0.388 |
| SIZE_6_TH10 | 0.625 | 0.140 | 2.400 | 2.400 | 2.400 | 1.003 | 0.748 | 0.575 |
| SIZE_4_TH10 | 0.491 | 0.131 | 2.154 | 2.154 | 2.154 | 0.800 | 0.562 | 0.441 |

| | d375 | d574 | d568 | d598 | d596 | d616 | d615 | d595 |
|---|---|---|---|---|---|---|---|---|
| SIZE_1P5_TH10 | 0.130 | 0.130 | 0.560 | 0.830 | 0.200 | 0.200 | 0.150 | 0.150 |
| SIZE_3_TH10 | 0.150 | 0.150 | 0.675 | 1.100 | 0.390 | 0.390 | 0.310 | 0.310 |
| SIZE_6_TH10 | 0.077 | 0.077 | 0.825 | 1.378 | 0.390 | 0.390 | 0.310 | 0.310 |
| SIZE_4_TH10 | 0.142 | 0.142 | 0.737 | 1.192 | 0.390 | 0.390 | 0.310 | 0.310 |

Figure 13c (BOTTOM) Dimensions That Change According To Thickness

| | d0 | d593 | d612 |
|---|---|---|---|
| SIZE_6_TH8 | 0.501 | 0.108 | 0.108 |
| SIZE_6_TH10 | 0.580 | 0.177 | 0.177 |
| SIZE_6_TH12P5 | 0.659 | 0.256 | 0.256 |
| SIZE_6_TH15 | 0.747 | 0.344 | 0.344 |
| SIZE_6_TH17P5 | 0.845 | 0.442 | 0.442 |
| SIZE_6_TH20 | 0.943 | 0.540 | 0.540 |
| SIZE_1P5_TH8 | 0.480 | 0.108 | 0.108 |
| SIZE_1P5_TH10 | 0.559 | 0.177 | 0.177 |
| SIZE_1P5_TH12P5 | 0.638 | 0.256 | 0.256 |
| SIZE_1P5_TH15 | 0.726 | 0.344 | 0.344 |
| SIZE_1P5_TH17P5 | 0.824 | 0.442 | 0.442 |
| SIZE_1P5_TH20 | 0.922 | 0.540 | 0.540 |
| SIZE_3_TH8 | 0.480 | 0.108 | 0.108 |
| SIZE_3_TH10 | 0.559 | 0.177 | 0.177 |
| SIZE_3_TH12P5 | 0.638 | 0.256 | 0.256 |
| SIZE_3_TH15 | 0.726 | 0.344 | 0.344 |
| SIZE_3_TH17P5 | 0.824 | 0.442 | 0.442 |
| SIZE_3_TH20 | 0.922 | 0.540 | 0.540 |
| SIZE_4_TH10 | 0.564 | 0.177 | 0.177 |
| SIZE_4_TH12P5 | 0.643 | 0.256 | 0.256 |

Figure 13d

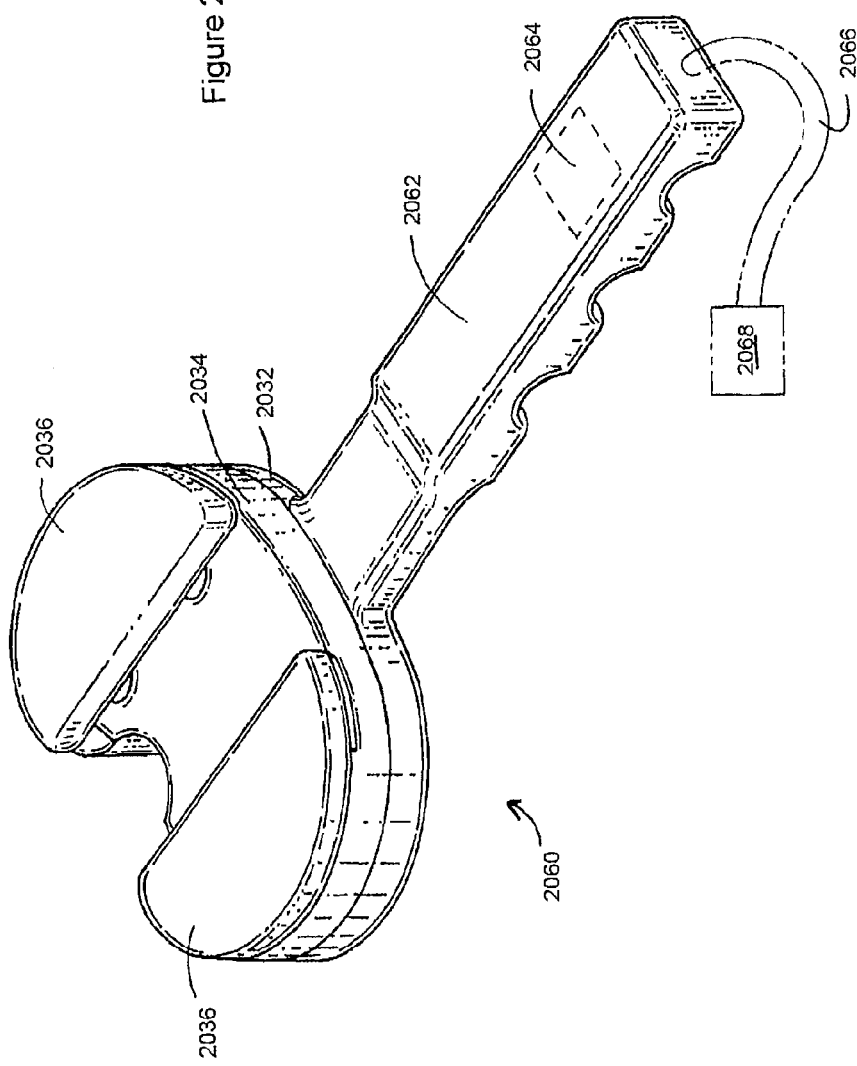

DEVICE AND METHOD OF SPACER AND TRIAL DESIGN DURING JOINT ARTHROPLASTY

PRIORITY CLAIM

The present application is a Continuation of U.S. patent application Ser. No. 13/406,159, filed Feb. 27, 2012, now U.S. Pat. No. 8,656,790, which is a Continuation of U.S. patent application Ser. No. 11/393,098, filed Mar. 29, 2006, now U.S. Pat. No. 8,141,437. U.S. patent application Ser. No. 11/393,098, filed Mar. 29, 2006 and U.S. patent application Ser. No. 13/406,159, filed Feb. 27, 2012 are incorporated herein by reference.

BACKGROUND

1. Technical Field

The present disclosure relates to joint replacement, and more particularly, to a spacer block used to provide data to assist in selecting the size of a trial implant.

2. Related Applications

This application incorporates by reference U.S. Patent Application Publication No. 2007/0233267, entitled "Application of Neural Networks to Prosthesis Fitting and Balancing in Joints," and U.S. Patent Application Publication No. 2007/0239165, entitled "Device and Method of Spacer and Trial Design During Joint Arthroplasty."

3. Related Art

Some medical conditions may result in the degeneration of a human joint, causing a patient to consider and ultimately undergo joint replacement surgery. The long-term success of the surgery oftentimes relies upon the skill of the surgeon and may involve a long, difficult recovery process.

The materials used in a joint replacement surgery are designed to enable the joint to move like a normal joint. Various prosthetic components may be used, including metals and/or plastic components. Several metals may be used, including stainless steel, alloys of cobalt and chrome, and titanium, while the plastic components may be constructed of a durable and wear resistant polyethylene. Plastic bone cement may be used to anchor the prosthesis into the bone, however, the prosthesis may be implanted without cement when the prosthesis and the bone are designed to fit and lock together directly.

To undergo the operation, the patient is given an anesthetic while the surgeon replaces the damaged parts of the joint. For example, in knee replacement surgery, the damaged ends of the bones (i.e., the femur and the tibia) and the cartilage are replaced with metal and plastic surfaces that are shaped to restore knee movement and function. In another example, to replace a hip joint, the damaged ball (i.e., the upper end of the femur) is replaced by a metal ball attached to a metal stem fitted into the femur, and a plastic socket is implanted into the pelvis to replace the damaged socket. Although hip and knee replacements are the most common, joint replacement can be performed on other joints, including the ankle, foot, shoulder, elbow, fingers and spine.

As with all major surgical procedures, complications may occur. Some of the most common complications include thrombophlebitis, infection, and stiffness and loosening of the prosthesis. While thrombophlebitis and infection may be treated medically, stiffness and loosening of the prosthesis may require additional surgeries. One technique utilized to reduce the likelihood of stiffness and loosening relies upon the skill of the physician to align and balance the replacement joint along with ligaments and soft tissue intraoperatively, i.e., during the joint replacement operation.

During surgery, a physician may choose to insert one or more temporary components. For example, a first component known as a "spacer block" is used to help determine whether additional bone removal is necessary or to determine the size of the "trial" component to be used. The trial component then may be inserted and used for balancing the collateral ligaments, and so forth. After the trial component is used, then a permanent component is inserted into the body. For example, during a total knee replacement procedure, a femoral or tibial spacer block and/or trial may be employed to assist with the selection of appropriate permanent femoral and/or tibial prosthetic components, e.g., referred to as a tibia insert.

While temporary components such as spacers and trials serve important purposes in gathering information prior to implantation of a permanent component, one drawback associated with temporary components is that a physician may need to "try out" different spacer or trial sizes and configurations for the purpose of finding the right size and thickness, and for balancing collateral ligaments and determining an appropriate permanent prosthetic fit, which will balance the soft tissues within the body. In particular, during the early stages of a procedure, a physician may insert and remove various spacer or trial components having different configurations and gather feedback, e.g., from the patient. Several rounds of spacer and/or trial implantation and feedback may be required before an optimal component configuration is determined. However, when relying on feedback from a sedated patient, the feedback may not be accurate since it is subjectively obtained under relatively poor conditions. Thus, after surgery, relatively fast degeneration of the permanent component may result.

Some previous techniques have relied on using sensors that are coupled to a temporary mechanical component to collect data. In these systems, the gathered information is limited to the location of the sensors. Other systems require a physician to perform a number of different tests to obtain usable data.

SUMMARY

A spacer block is provided that includes a first body piece and a second body piece positioned on top of the first body piece. The first piece includes a plurality of sensors that measure forces, such as dynamic contact forces, between the first and second body pieces. The spacer block includes a processor that includes a memory. The processor is operatively coupled to the plurality of sensors to receive data therefrom. In one aspect, at least one chim may be positioned on top of the second body piece.

In another aspect, the first body piece includes a plurality of structurally integrated poles extending vertically upward such that distal ends of the poles are calibrated to be in contact with the second body piece. The sensors may comprise a plurality of strain gauges positioned on the poles. The strain gauges are operatively connected to the processor and are adapted to measure compression, tension, and bending forces between the first and second body pieces. Each pole is positioned such that the strain gauges will measure forces between the first and second body pieces due to contact forces exerted on the associated chim.

In still another aspect, the spacer block includes a transmitter that is operatively connected to the processor. The transmitter is adapted to transmit data from the processor to ta remote receiver.

In yet another aspect, the spacer block includes a handle detachably connected to the spacer block for manipulation of the spacer block. The spacer block and the handle include features to allow an electrical connection therebetween when the handle is connected to the spacer block. The handle may include a transmitter operatively connected to the processor through the electrical connection, wherein data from the processor is transmitted to a remote receiver, when the handle is connected to the spacer block. Alternatively, the handle may include a hard wired connection to a receiver such that data from the processor can be sent to the receiver, through the handle, when the handle is connected to the spacer block.

In still another aspect, the spacer block includes a handle that is integrally formed with the spacer block. Similarly to the detachable handle, the integrally formed handle may include a transmitter operatively connected to the processor, wherein data from the processor is transmitted to a remote receiver. Alternatively, the handle may include a hard wired connection to a receiver such that data from the processor can be transmitted to the receiver, through the handle.

Other systems, methods, features and advantages of the invention will be, or will become, apparent to one with skill in the art upon examination of the following figures and detailed description. It is intended that all such additional systems, methods, features and advantages be included within this description, be within the scope of the invention, and be protected by the following claims.

BRIEF DESCRIPTION OF THE DRAWINGS

The discussion below may be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIG. 12l is a twelfth schematic of structures used in a force monitoring system.

FIG. 13a is a table providing example dimensions for the structures of FIG. 12.

FIG. 13b is a second table providing example dimensions for the structures of FIG. 12.

FIG. 13c is a third table providing example dimensions for the structures of FIG. 12.

FIG. 13d is a fourth table providing example dimensions for the structures of FIG. 12.

FIG. 20 is a perspective view of a spacer block having an integrally formed handle.

DETAILED DESCRIPTION

Figure 1:
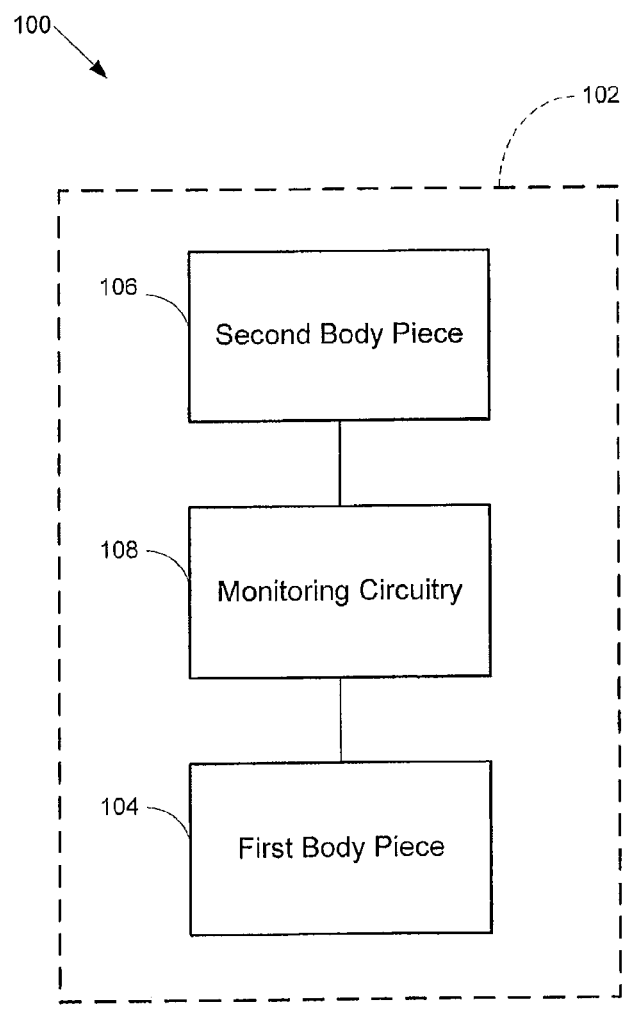
FIG. 1 is a diagram of a system that monitors forces between two bearing surfaces.

FIG. 1 is a diagram of a system 100 that monitors one or more forces between bearing surfaces, such as one or more dynamic contact forces, such as the force at contact between two bearing surfaces, or a dynamic contact force related measurement such as a strain, stress, torsion, and/or pressure. An enclosure 102 may comprise first body piece 104 (e.g., lower block) and second body piece 106 (e.g., upper block), each body piece comprising an inner surface and an outer surface. The first body piece and second body piece 104 and 106 are configured to mate together. The inner surface of first body piece 104 may comprise one or more protrusions, such as poles, posts, or beams, which are preferably integrally formed and which extend from a bearing surface. A portion of the inner surface of first body piece 104 may be recessed to receive some or all of monitoring circuitry 108. Alternatively, first body piece 104 may not include a recessed portion and monitoring circuitry 108 may overlay the inner surface of first body piece 104. One or more portions of the inner surface of second body piece 106 may be recessed to receive the one or more poles of first body piece 104 and monitoring circuitry 108 when the mating body pieces are fit together.

When fit together, the external surfaces of first body piece and second body piece 104 and 106 may comprise the bearing surfaces of force monitoring system 100. As forces are applied to or removed from the bearing surfaces, a force representing the algebraic summation of one or more forces, may be transferred from the bearing surfaces to one or more of the poles. The transferred force may cause a measurable mechanical motion in one or more of the poles, such as a displacement and/or deformation. The mechanical motion may comprise rotational motion and/or compression and/or expansion in the longitudinal and/or latitudinal direction of the one or more poles. Monitoring circuitry 108 senses and/or models and/or analyzes the mechanical motion of the one or more poles. Data representative of the mechanical motion of the one or more poles may be used to determine whether modifications to the structure(s) exerting the sensed and/or modeled and/or analyzed dynamic contact force is required.

Figure 2:
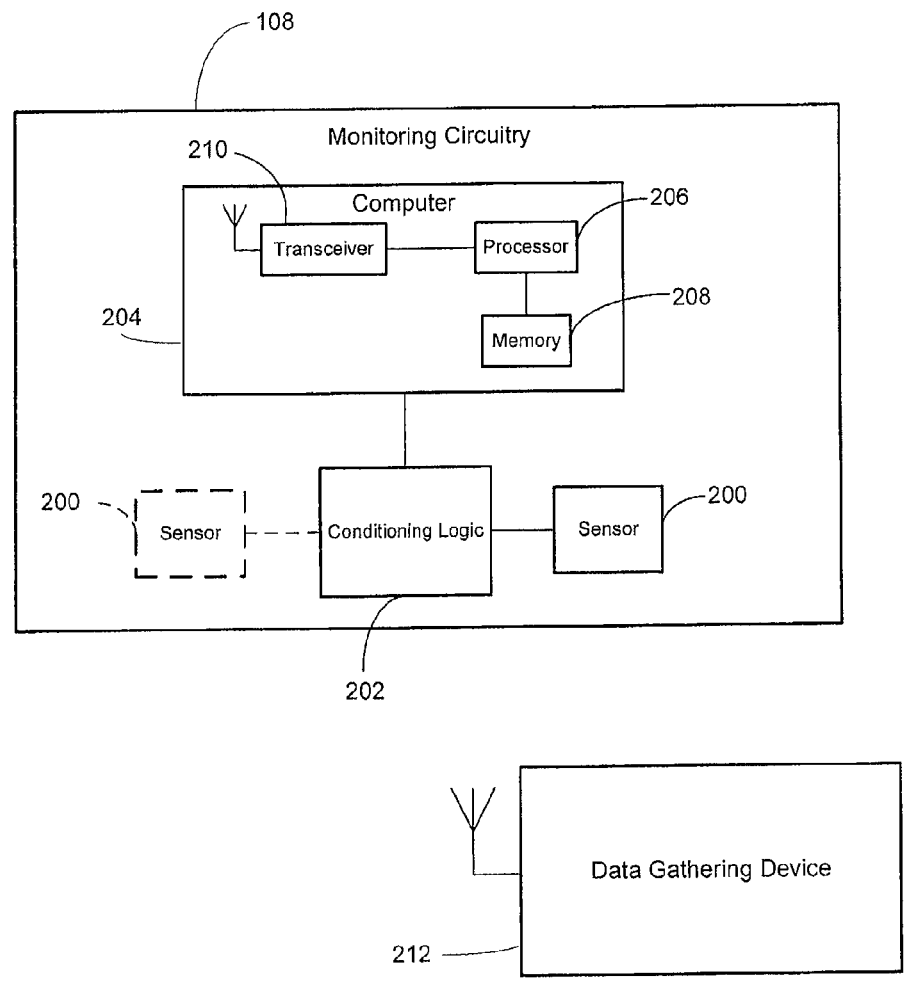
FIG. 2 is a block diagram of monitoring circuitry.

FIG. 2 is a block diagram of monitoring circuitry 108. Monitoring circuitry 108 comprises one or more sensors 200, programmable conditioning logic 202, and computer 204. The one or more sensors 200 may be single or multifunction sensors that are disposed on the surface of one or more of the poles and which detect or measure a mechanical motion resulting from the application of dynamic contact forces on enclosure 102. The one or more sensors 200 convert the detected or measured motion into an electrical signal in a time period which occurs at or near the same rate of time perceived by a human, such as real-time. Alternatively, the one or more sensors 200 may covert the detected or measured motion into an electrical signal in batches such that the conversions occur in delayed time. The electrical signal may have an amplitude that varies with the amount of displacement and/or deformation of the one or more posts. Alternatively, the electrical signal may comprise a discontinuous stream of on/off pulses.

The sensed electrical signals generated by the one or more sensors 200 may be supplied to conditioning logic 202 through a signal medium, such as a flexible signal medium. The flexible signal medium may comprise a plurality of conductors affixed to or enclosed within a continuous bendable material, such as a flexible printed circuit. The flexible signal medium may overlay some or the entire inner surface of first body piece 104, and may move relative to the movement of first body piece 104 and/or second body piece 106. Alternatively, the sensed electrical signals may be supplied to control logic 202 through a discrete wired signal medium and/or a wireless signal medium.

The sensed electrical signals generated by the one or more sensors 200 may be conditioned by conditioning logic 202 to improve the manner in which the signal content is further processed by monitoring circuitry 108 and/or to improve the quality of the corresponding data content. Signal conditioning may include selecting two or more signals received from sensors 200 and combining the selected signals into a single channel (e.g., multiplexing the received signals one after another into a serial signal) and/or perform logic operations on all or a portion of the received signal (e.g., converting a voltage and/or current signal into data representing an amount of displacement/deformation, or passing the received signal through a Wheatstone bridge) and/or removing a continuous noise signal from the received electrical signal (e.g., filtering) and/or enlarging the waveform of the received intermediate signal or signals (e.g., amplification). The signal conditioning logic 202 may comprise hardware and/or software that is capable of running on one or more processors in conjunction with one or more operating systems.

Computer 204 may be configured to receive data, such as sensed electrical signals, directly from sensors 200 or to receive a conditioned signal. Computer 204 may comprise processor 206, memory (volatile or non-volatile) 208, and/or transceiver 210. Processor 206 may vary in size and performance depending on the tasks. Processor 206 may perform control operations by transmitting control signals to conditioning logic 202. Control operations may comprise determining which electrical signals are multiplexed, and/or altering an amount of noise attenuation, and/or varying an amplifier gain factor. The signals received at processor 206 may be stored in memory 208 without undergoing any additional processing by processor 206 (e.g., raw data).

Alternatively, processor 206 may perform in real-time or delayed time arithmetic and/or logic operations on the received signals to model the forces between the bearing surfaces. The modeled data may be used to determine the magnitude of a dynamic force exerted on different locations of enclosure 102 under different conditions, or to determine where on the enclosure a dynamic contact force is exerted. The modeled data may be stored in memory 208 via a bidirectional bus.

Transceiver 210 is configured to receive from processor 206 data, such as modeled data and/or sensed electrical signals, and forward the received data to a data gathering device 212. Data gathering device 212 may be a fixed device, such as a computer, or a mobile device, such as a handheld computer, personal digital assistant ("PDA"), and/or a mobile communications device. Prior to transmitting data, transceiver 210 may transmit a control message to data gathering device 212. The message may inform data gathering device 212 that data will be transmitted. Data gathering device 212 may then acknowledge its receipt of the control message by sending an acknowledgement message back. The acknowledgement message may inform transceiver 210 to begin transmitting data.

Transceiver 210 may comprise a port configured to receive a transmission wire and transmit/receiver data sequentially or simultaneously through multiple protocols. These protocols may include Extensible Markup Language ("XML"), Hyper Text Transfer Protocol ("HTTP"), Transmission Control Protocol/Internet Protocol ("TCP/IP"), as well as other public or proprietary protocols developed in house or by others. Transceiver 210 may additionally be coupled to an antenna and communicate with data gathering devices through wireless protocols. These protocols may include 802.11b, 802.11j, 802.11g, other 802 wireless protocols, Bluetooth®, Zigbee®, or other developing wireless protocols. Based on the modeled data, processor 206 may control the frequency with which transceiver 210 forwards data to a data gathering device.

Figure 3:
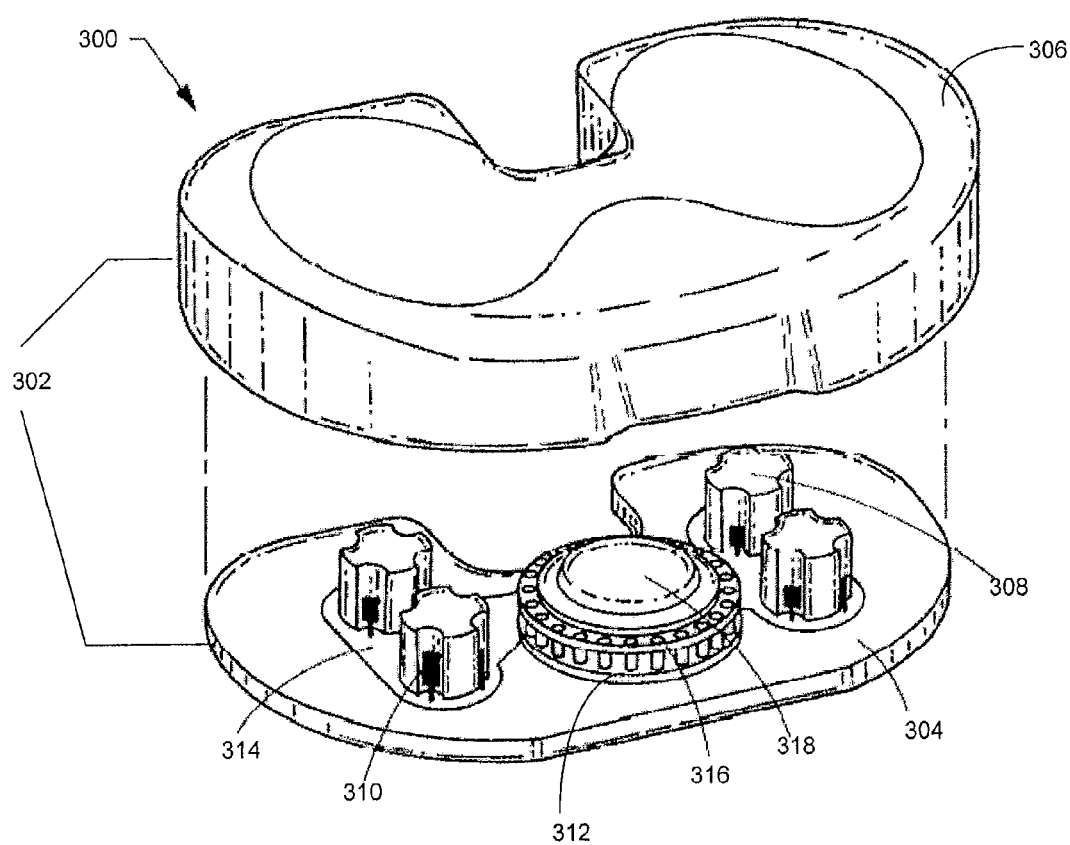
FIG. 3 is a diagram of a system that monitors forces between bearing surfaces.

FIG. 3 illustrates an exemplary system 300 that may be used as a prosthetic joint spacer block, trial, or insert used to monitor a dynamic contact force between two bearing surfaces, such as between the femur and tibia bones. Force monitoring system 300 comprises enclosure 302 having a first body piece 304 and a second body piece 306. The first body piece and second body piece 304 and 306 may generally have a U-shape, although other shapes may be used. The outer surfaces of body pieces 304 and/or 306 may be substantially flat or may be customized to receive a particular contact surface. In FIG. 3, second body piece 306 is customized to receive a particular contact surface. Recessed portion 320 is configured with concave surfaces to receive the rounded bumps of a reconstructed femur bone, the artificial medial and lateral condyles. The inner surface of second body piece 306 may comprise one or more recesses configured to receive poles 308 of first body piece 304, such that first body piece and second body piece 304 and 306 may be mated together.

In FIG. 3, a plurality of poles 308 are symmetrically spaced on the inner surface of first body piece 304. Poles 308 are aligned with the underside of second body piece 306. Where second body piece 306 includes a recessed exterior surface, such as to receive condyle portions, poles 308 are aligned with the underside of the plane which passes through the lowest point of the second body piece's 306 condyle recesses. Poles 308 are configured such that they contact, without detectible load transfer, the underside of the condyle recesses when no force is applied to the mated first and second body pieces 304 and 306. Application of a Force to first and/or second body pieces 304 and 306 may cause the second body piece 306 to push against the poles 308 thereby causing the poles 308 to undergo a detectible mechanical motion. Although poles 308 are illustrated as having a flat upper surface, poles 308 may be configured with a curved surface that mirrors a curved inside surface of second body piece 306 such that there is a uniform distance between the inside surface of second body piece 306 and the top of poles 308.

Poles' 308 geometry relates to an applied strain, and related measurements, as the strain is dependent upon the cross-sectional area of poles 308. Poles' 308 geometry includes a plurality of grooves into which one or more sensors 310 may be disposed. The one or more sensors 310 may be disposed on the surface of poles 308 within the grooved portions. The distance from the base of corresponding pole may for example be about 3 mm. Placement of the one or more sensors 310 within the pole grooves may protect the one or more sensors 310 when first body piece and second body piece 304 and 306 are mated together. Additionally, when the body pieces are mated together, a space may exist between the non-grooved portion of pole 308 and a corresponding receiving recess to permit the first and/or second body pieces 304 and 306 to freely move. This space, for example, may be about 0.015 inches.

One or more sensors 310 may comprise a plurality of strain gages adapted to generate a voltage in response to dynamic contact forces transferred from the bearing surfaces to poles 308. Strain gauges are configured to measure an amount of deformation of a body due to an applied force. More specifically, strain gauges are configured to measure or detect a change of length in a body with respect to the original length of that body. Depending on the number of sensors 310 disposed on a pole 308 and the orientation of the sensors 310, a compression, extension, rotation, and/or bending of a pole 308 may be detected. Data detected or measured by sensors 310, representing a compression; extension; rotation; and/or bending of a pole 308, may be provided to conditioning logic 312 through signal medium 314. Signal medium 314 may generally conform to the shape of first body piece 304 but with a smaller length and width. Signal medium 314 may comprise a plurality of conductors affixed to a flexible continuous bendable material such as a flexible printed circuit. A plurality of holes or openings may be provided in signal medium 314 through which poles 308 may be received. Signal medium 314 may lie loosely on top of the inner surface of first body piece 304, its position being maintained by poles 308 and the remainder of the monitoring circuitry. Alternatively, the signal medium may be affixed to the inner surface of first body piece 304 in a few locations such as to permit signal medium to flex relative to the movement of first assembly 304 and/or second assembly 306.

Conditioning logic 312 may comprise hardware connected through a printed circuit board. Conditioning logic 312 may communicate with flexible signal medium 314. To allow for easy assembly and/or removal, a connector may couple conditioning logic 312 to flexible signal medium 314. For example, an OMRO 0.5-pitch Lock FPC Connector may be affixed to the printed circuit board and used to couple conditioning logic 312 to flexible signal medium 314.

In FIG. 3, one sensor is affixed to each groove of poles 308 (e.g. a total of 16 sensors), although more or less sensors or poles could be used. Conditioning logic 312 processes the data through a multiplexer, such as a 16-channel multiplexer, and routes the multiplexed data to a series of amplifiers. To increase the amplification range, amplifiers may be cascaded in series. For example, a set of two amplifiers each with a gain factor of 100 may be cascaded in series to achieve a total gain factor amplification of 10000. After amplification, the data is collected by computer 316 where it may be stored or transmitted to a data gathering device. An antenna may be disposed around the periphery of the printed circuit board and is preferably provided to transmit and receive data.

Computer 316 may comprise battery 318. Battery 318 provides power to computer 316, conditioning logic 312, and/or sensors 310. In this embodiment, computer 316 transmits and receives data to/from conditioning logic 312 via a bidirectional bus. The transmission and receipt of data between computer 316 and conditioning logic 312 may occur sequentially or simultaneously.

Figure 4:
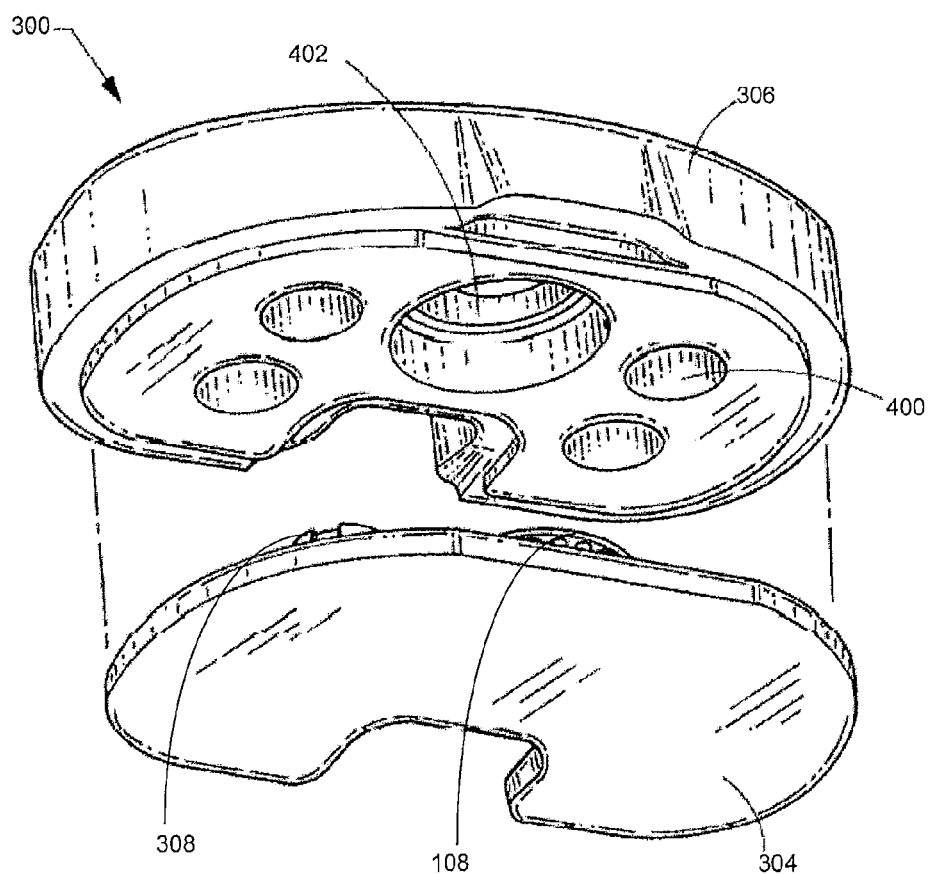
FIG. 4 is bottom perspective view of the system that monitors forces between bearing surfaces of FIG. 3.

FIG. 4 is a bottom perspective view of force monitoring system 300. In FIG. 4, recesses 400 are integrally formed in second body piece 306 for receiving poles 308 of first body piece 304. A central recess 402 is integrally formed in second body piece 306 for receiving monitoring circuitry 108.

Figure 5:
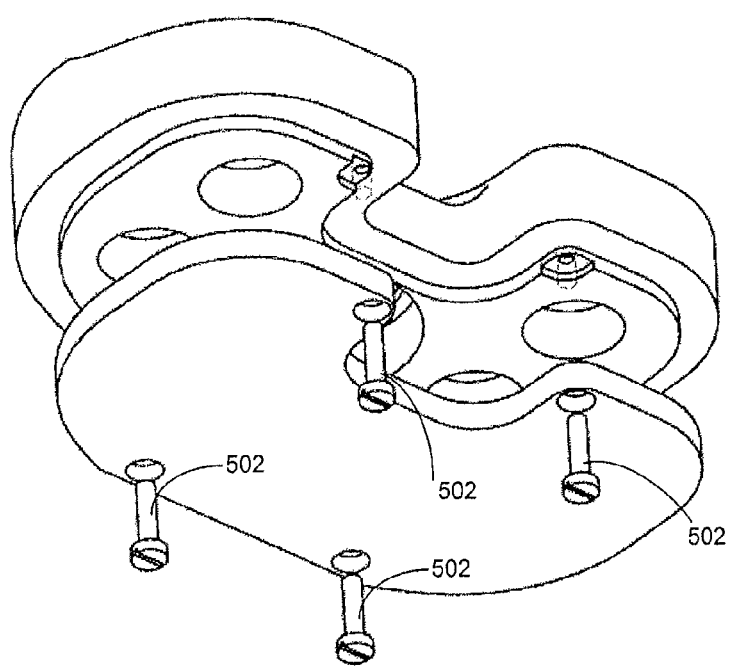
FIG. 5 is a diagram of a closure mechanism used in a system that monitors a force between bearing surfaces.

To keep first body piece and second body piece 304 and 306 mated together each body piece may be configured to receive one or more fasteners along its outer rim. In FIG. 5, a plurality of screw fasteners 502 are used to secure first body piece and second body piece 304 and 306. The plurality of screw fasteners 502 may be configured to allow second body piece 306 to move downward while limiting its upward motion to about its position when no force is exerted against the body pieces. Alternatively, instead of screw fasteners 502, first body piece and second body piece may be configured with mating snap latches on their out rim. The snap latches may operate in a similar manner to the screw fasteners 502—permitting second body piece 306 to move downward while limiting its upward motion.

Figure 6:
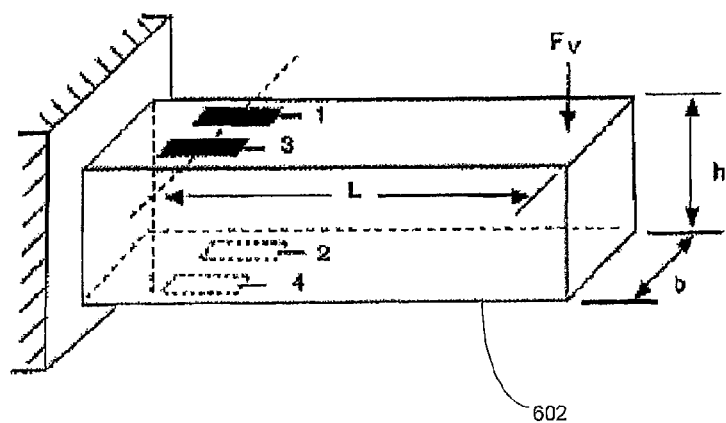
FIG. 6 is a sensor configuration diagram.

The orientation of the sensors along with the principles of beam theory may be utilized to collect data representing the mechanical motion of the one or more poles 308 when the first body piece and second body piece are force against one another. FIG. 6 is a sensor configuration diagram for measuring or detecting bending. This configuration may be used to measure or detect the bending of a pole 308 of force monitoring system 300. To detect bending, two or more sensors are mounted on opposite sides of a pole in a plane that is perpendicular to an applied force, $F_y$. In FIG. 6, two sensors are disposed on each side of pole 602, 1 and 3 and 2 and 4, respectively. The inclusion of extra sensors increases the accuracy of the measured or detected bending. As pole 602 bends, sensors 1 and 3 and 2 and 4 are stressed and generate a signal that may be analyzed to determine the amount of movement of pole 602.

Figure 7:
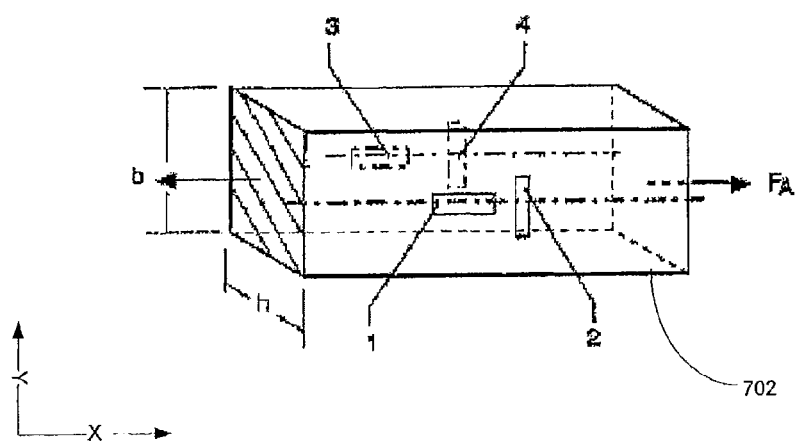
FIG. 7 is a second sensor configuration diagram.

FIG. 7 is a sensor configuration diagram for measuring or detecting a deformation along a pole's axis, such as an expansion or contraction. This configuration may be used to measure or detect an expansion or contraction of a pole 308 of force monitoring system 300. Axial deformation may be measured or detected by disposing one or more sensors on a pole 702 in a plane parallel to a force, $F_A$. In FIG. 7, sensors 1 and 3 are oriented to measure or detect an axial deformation in the X-direction. Alternatively or additionally, one or more sensors may be disposed on pole 702 in a plane perpendicular to force $F_A$ and used to measure or detect an expansion or contraction in the Y-direction. In FIG. 7, sensors 2 and 4 are oriented to measure or detect this type of expansion or contraction.

Figure 8:
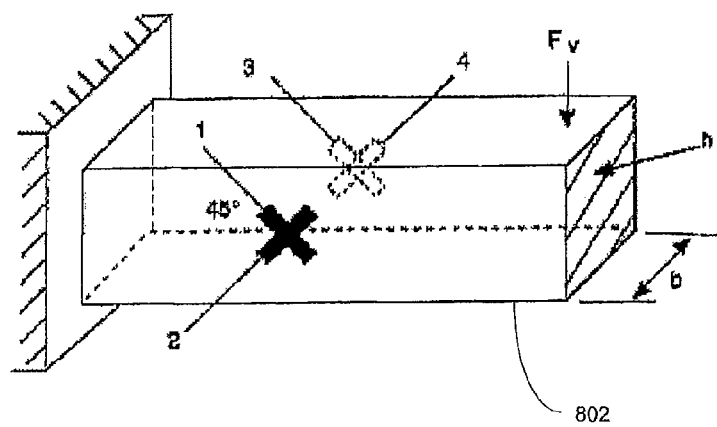
FIG. 8 is a third sensor configuration diagram.

FIG. 8 is a sensor configuration diagram for measuring or detecting a strain that produces a distortion or deformation of pole 802 without a volumetric change, such as a shear strain. This configuration may be used to measure or detect a shear strain of a pole 308 of force monitoring system 300. To measure shear strain, two sensors are disposed on pole 802 at an angle with respect to one another, such as about a 45° angle. When a measurement of the sensors is compared to a prior measurement and it is determined that the pole has been deformed in more than one direction, a shear force has been detected. In addition to measuring shear strain, the configuration illustrated in FIG. 8 may be used to measure or detect an axial or bending strain component.

Figure 9:
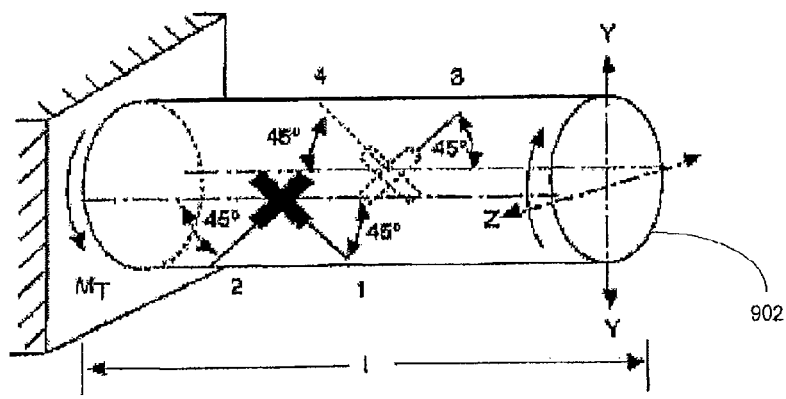
FIG. 9 is a fourth sensor configuration diagram.

FIG. 9 is a sensor configuration diagram for measuring or detecting a strain that produces a rotation or twisting action, such as a torsional strain. This configuration may be used to measure or detect a torsional strain of a pole 308 of force monitoring system 300. Torsional strain may be measured or detected using a similar sensor configuration as that used to measure or detect a shear strain. Accordingly, two sensors are disposed on post 902 at an angle with respect to one another, such as about a 45° angle. As shown in FIG. 9, torsional strain measures a rotational force about a central axis. Although FIGS. 6-9 describe configurations for measuring or detecting individual strains, multiple sensors disposed in multiple configurations may be disposed on one or more poles to measure or detect one or a combination of bending, shear, and/or torsional strains.

Figure 10:
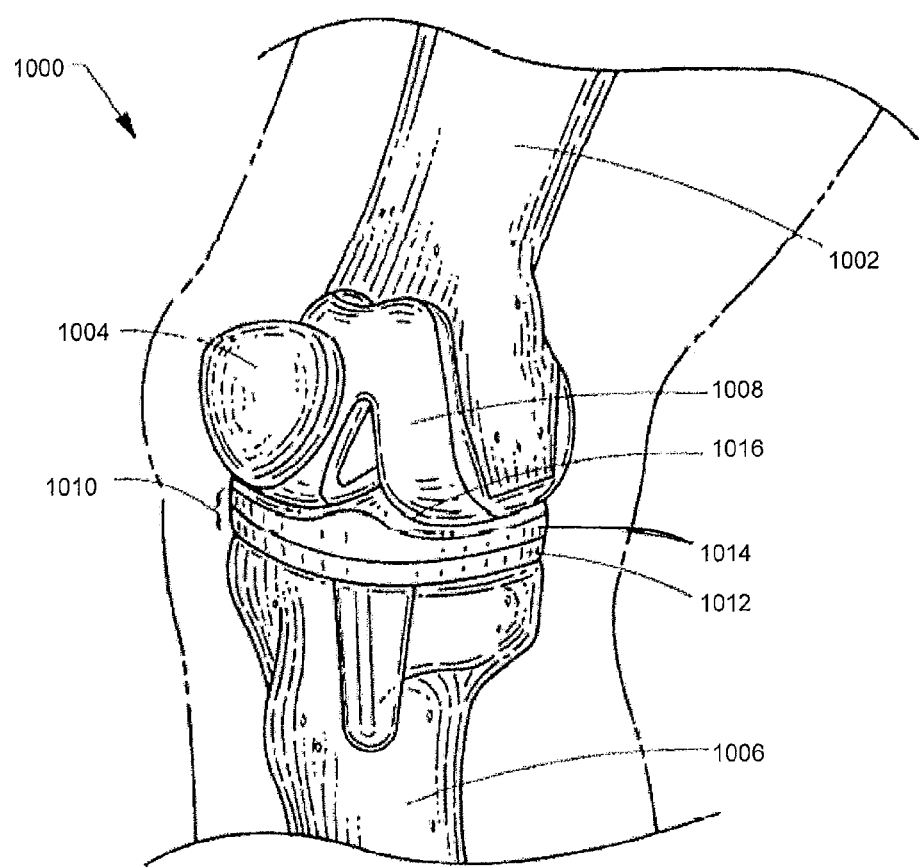
FIG. 10 is a diagram of a system that monitors a force between bearing surfaces incorporated into a prosthetic knee joint.

FIG. 10 is a diagram of a system that monitors a force between bearing surfaces in a prosthetic joint environment. In FIG. 10, human knee 1000 comprises femur 1002, patella 1004, tibia 1006, a plurality of ligaments (not shown), and a plurality of muscles (not shown). In this example, the prosthesis used during a total knee arthroplasty (TKA) procedure comprises femoral component 1008 and tibial component 1010. Tibial component 1010 may comprise tibial tray 1012 and force monitoring system enclosure 1014. Force monitoring system enclosure 1014 may be temporarily attached to tibial tray 1012. Alternatively, the enclosure may be integrally formed to provide bearing surfaces. Force monitoring system enclosure 1014 may comprise embedded circuitry and one or more sensors that are capable of acquiring data. The acquired data relates to dynamic contact forces and the location of the dynamic contact forces imposed upon force monitoring system enclosure 1014.

The materials used in a knee joint replacement surgery are designed to enable the joint to mimic the behavior of a normal knee. Femoral component 1008 may comprise a metal piece that is shaped similar to the end of a femur, e.g., having condyles 1016. Condyles 1016 are disposed in close proximity to a bearing surface of force monitoring system enclosure 1014, and preferably fit closely into corresponding concave surfaces of enclosure 1014. In preferred embodiments, femoral and tibial components 1008 and 1010 comprise several metals, including stainless steel, alloys of cobalt and chrome, titanium, or another suitable material. Plastic bone cement may be used to anchor permanent prosthetic components into femur 1002 and tibia 1006. Alternatively, the prosthetic components may be implanted without cement when the prosthesis and bones are designed to fit and lock together directly, e.g., by employing a fine mesh of holes on the surface that allow the femur 1008 and tibia 1006 to grow into the mesh to secure the prosthetic components to the bone.

As shown, femoral component 1008 preferably resides in close proximity to an exterior surface of force monitoring system enclosure 1014. Contact between femoral component 1008 and the exterior surface of enclosure 1014 generates a force exerted on enclosure 1014. The exerted force is transferred to one or more poles 308 (internal to enclosure 1014) and results in a deformation of one or more of poles 308. One or more sensors 310 embedded within enclosure 1014 sense the deformation and generate a representative output signal.

Figure 11:
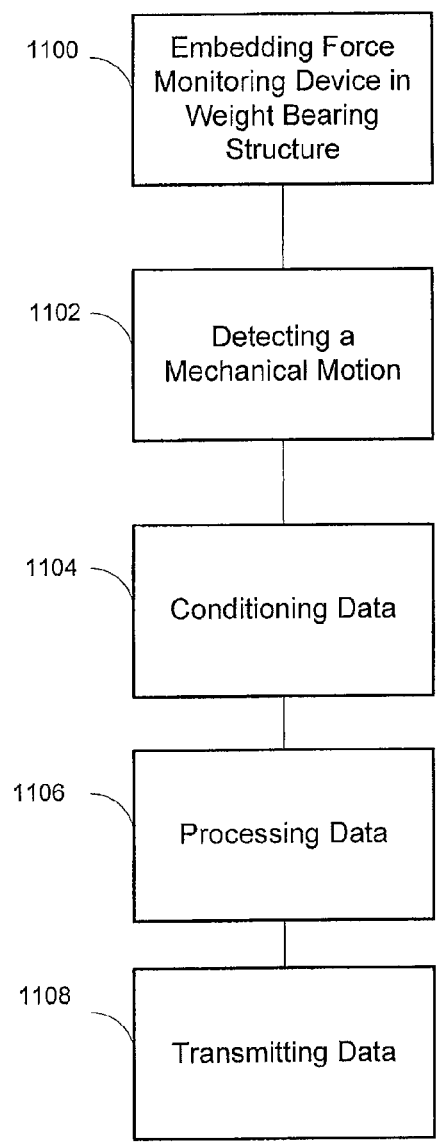
FIG. 11 is a flowchart of a system that monitors a force between bearing surfaces.

FIG. 11 is a flow diagram of a system that monitors a force between bearing surfaces. At act 1100, a monitoring device comprising at least one sensor and monitoring circuitry which is preferably embedded in the monitoring device is placed within a weight bearing structure. The at least one sensor may be disposed on an internal portion of the monitoring device's structure, such as a post. At act 1102, at least one sensor detects a mechanical motion in a portion of the monitoring device's structure, such as a mechanical motion of an internal post. The mechanical motion is preferably detected in real-time, and may indicate a rotational motion and/or a compression or extension in the longitudinal and/or latitudinal direction of the monitoring device's structure. At least one sensor generates an electrical signal, such as a voltage, responsive to the detection of the mechanical motion.

To assure a good quality measurement, the generated electrical signal is preferably conditioned at act 1104. In an example, conditioning of the electrical signal comprises combining one or more signals from at least one of the sensors, substantially attenuating a noise signal, converting the received electrical signal into a data representative of an amount of displacement/deformation of the monitoring device's structure, and/or multiplying the representative data signal by a static or variable gain.

At act 1106 the conditioned signal is processed by a computer. Processing the data may include performing arithmetic and/or logic operations on the conditioned data to model the force imposed on the bearing surfaces of the monitoring device. The modeled data is preferably stored in memory. The memory may be internal or external to the processing computer. The processing computer accesses the data stored in the memory to perform a statistical analysis.

The data modeled by the computer, the data representing the statistical analysis, and/or the conditioned data prior to any processing at act 1106 (e.g., raw data) may be transmitted at act 1108. The data may be transmitted to a data gathering device through a wired or wireless medium.

Some or all of the method of FIG. 11, in addition to the other methods described above, and/or neural network analyses as described in applicant's published U.S. Patent Application (No. 2007/0233267), entitled "Application of Neural Networks to Prosthesis Fitting and Balancing in Joints," may be encoded in a signal bearing medium, a computer readable medium such as a memory, programmed within a device such as one or more integrated circuits, or processed by a controller or a computer. If the method is performed by software, the software may reside in a memory resident to or interfaced to computer 316. Preferably the memory includes an ordered listing of executable instructions for implementing logical functions. A logical function may be implemented through digital circuitry, through source code, through analog circuitry, or through an analog source such as through an electrical, audio, or video signal. The software may be embodied in any computer-readable or signal bearing medium, for use by, or in connection with an instruction executable system, apparatus, or device. Such a system may include a computer-based system, a processor-containing system, or another system that may selectively fetch instructions from an instruction executable system, apparatus, or device that may also execute instructions.

A "computer-readable medium," "machine-readable medium," "propagated-signal medium," and/or "signal-bearing medium" comprise any means that contains, stores, communicated, propagated, or transports software for use by or in connection with an instruction executable system, apparatus, or device. The machine-readable medium may selectively be, but not limited to, an electronic, magnetic, optical, electro-magnetic, infrared, or semiconductor system, apparatus, device, or propagation medium. A non-exhaustive list of examples of a machine-readable medium would include: an electrical connections (e.g., electronic) having one or more wires, a portable magnetic or optical disk, a volatile memory such as a Random Access Memory "RAM" (electronic), a Read-Only Memory "ROM" (electronic), an Erasable Programmable Read-Only Memory (EPROM or Flash Memory) (electronic), or an optical fiber (optical). A machine-readable medium may also include a tangible medium upon which software is printed, as the software may be electronically stored as an image or in another format (e.g., through an optical scan), then compiled, and/or interpreted or otherwise processed. The processed medium may then be stored in a computer and/or machine memory.

Figure 12A:
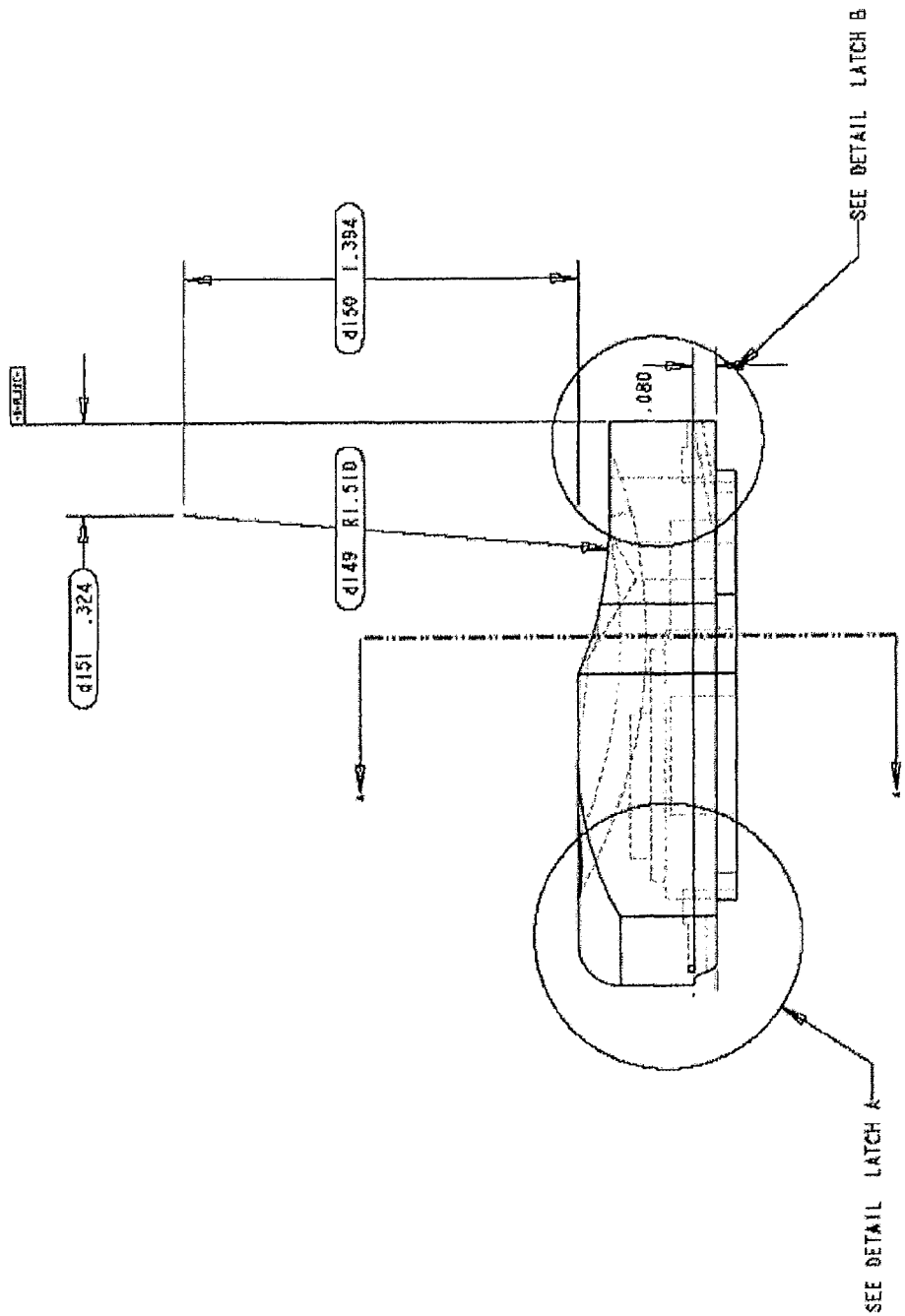
FIG. 12a is a schematic of structures used in a force monitoring system.
Figure 12B:
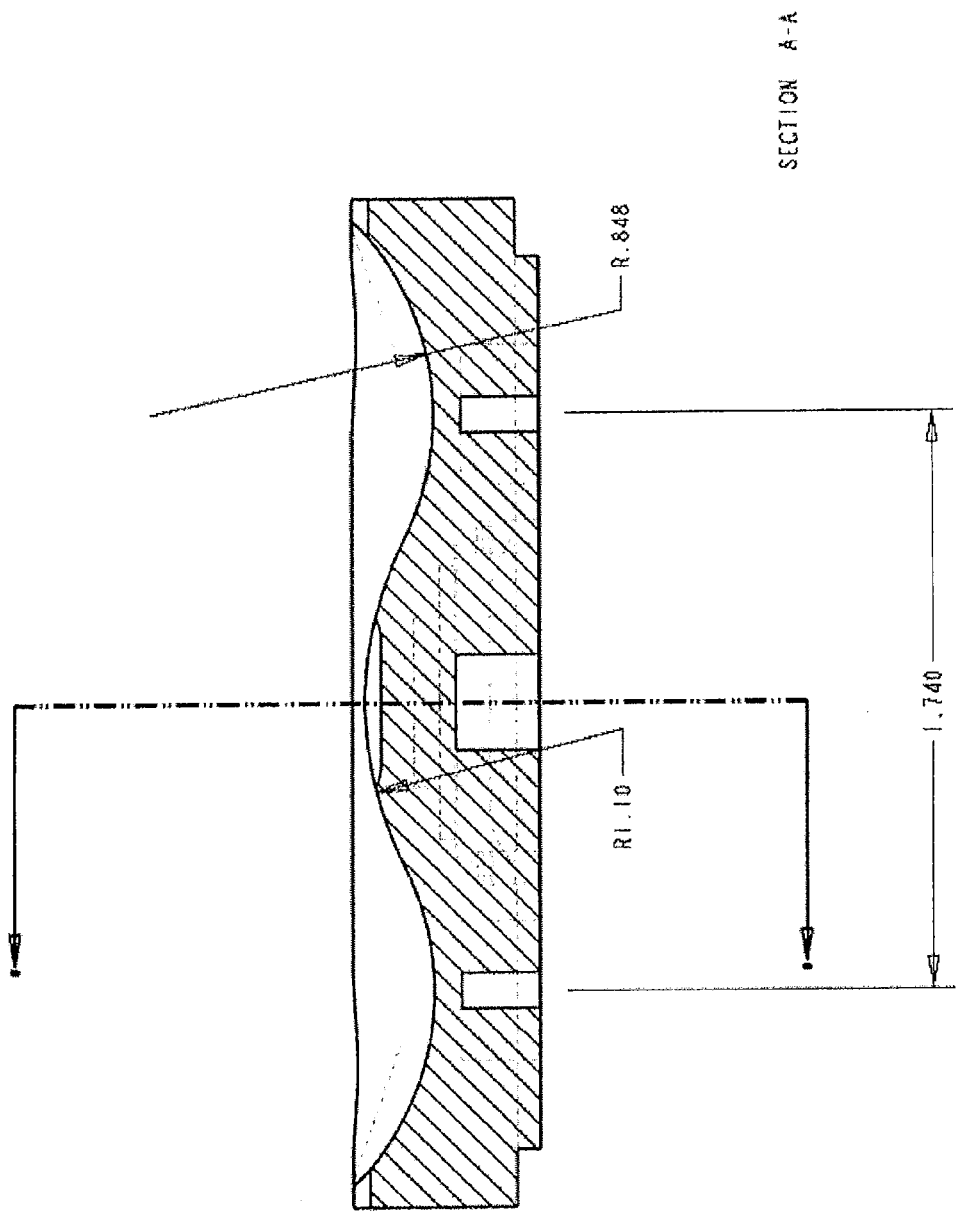
FIG. 12b is a second schematic of structures used in a force monitoring system.
Figure 12C:
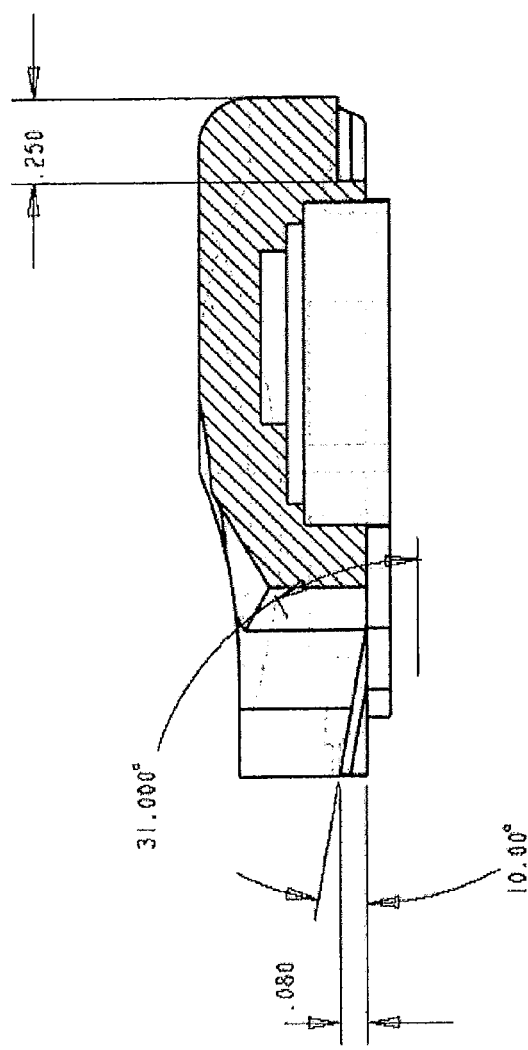
FIG. 12c is a third schematic of structures used in a force monitoring system.
Figure 12D:
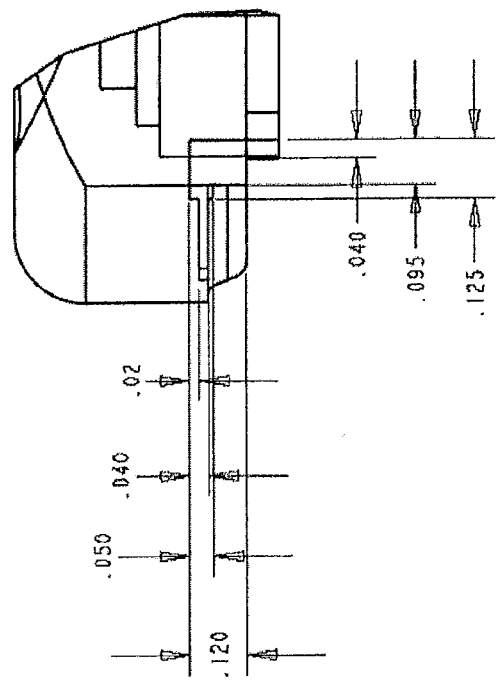
FIG. 12d is a fourth schematic of structures used in a force monitoring system.
Figure 12E:
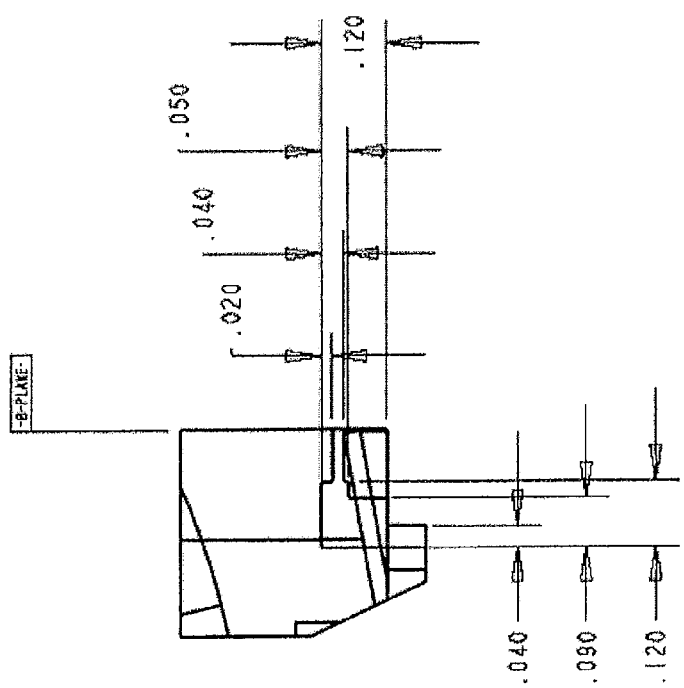
FIG. 12e is a fifth schematic of structures used in a force monitoring system.
Figure 12F:
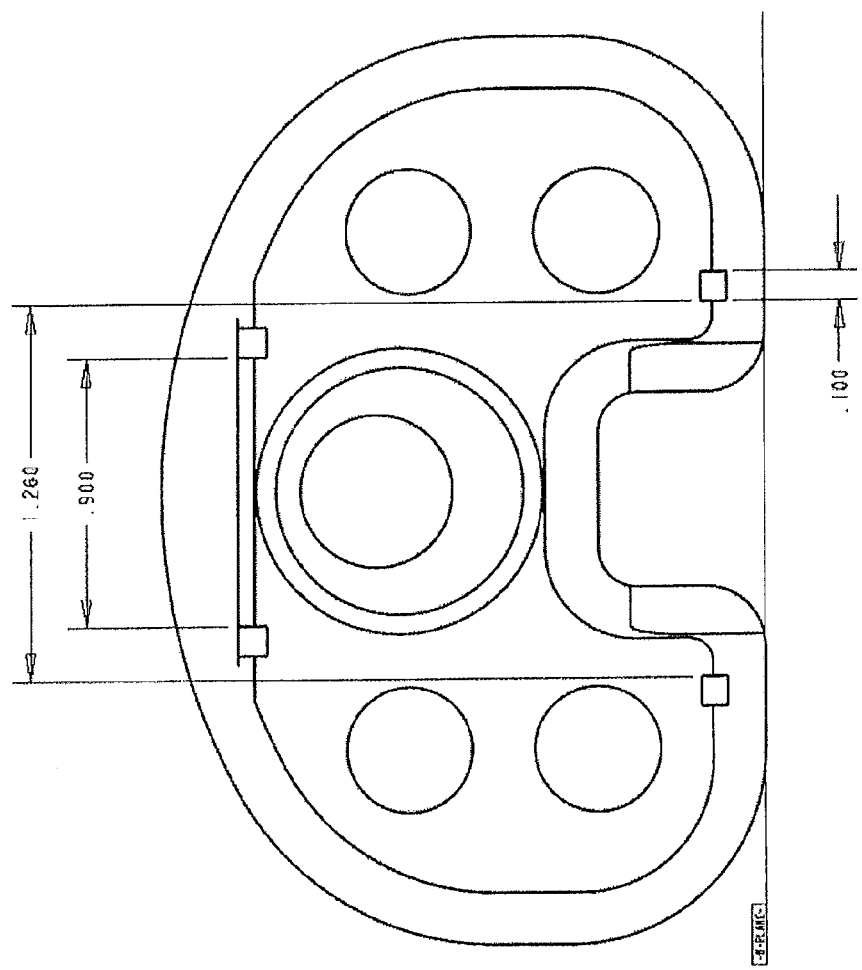
FIG. 12f is a sixth schematic of structures used in a force monitoring system.
Figure 12G:
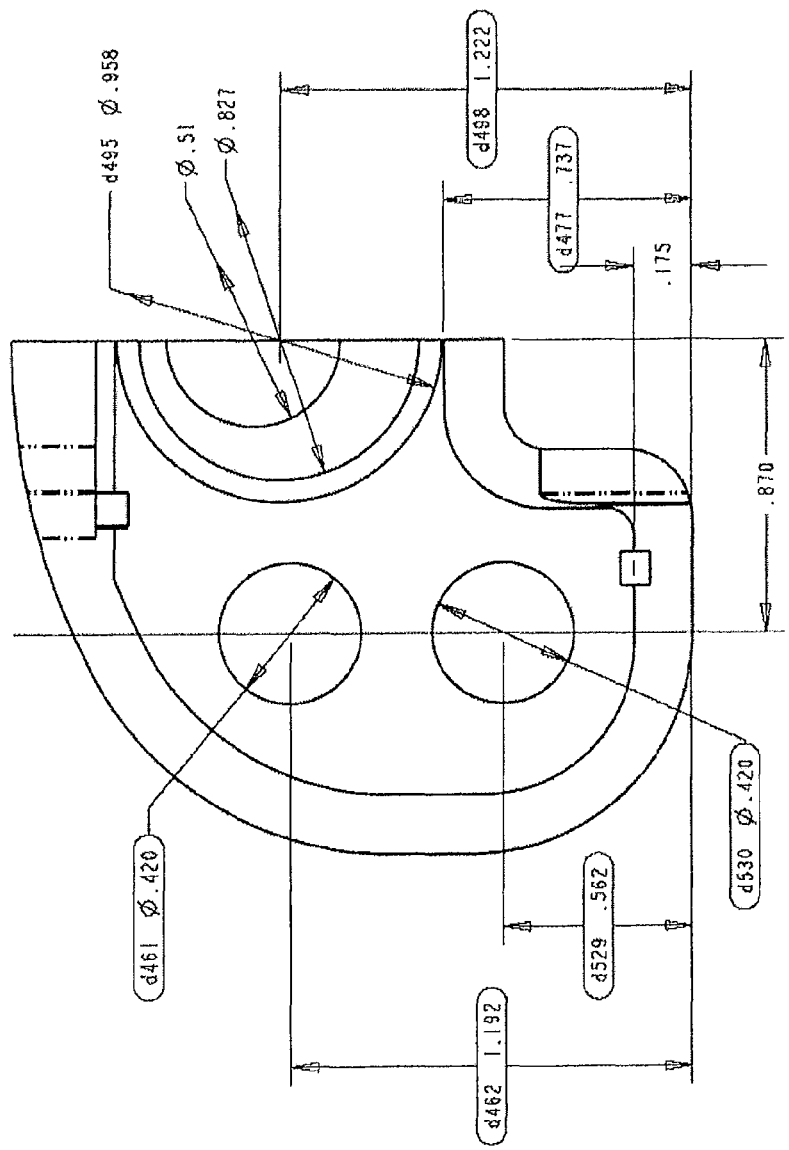
FIG. 12g is a seventh schematic of structures used in a force monitoring system.
Figure 12H:
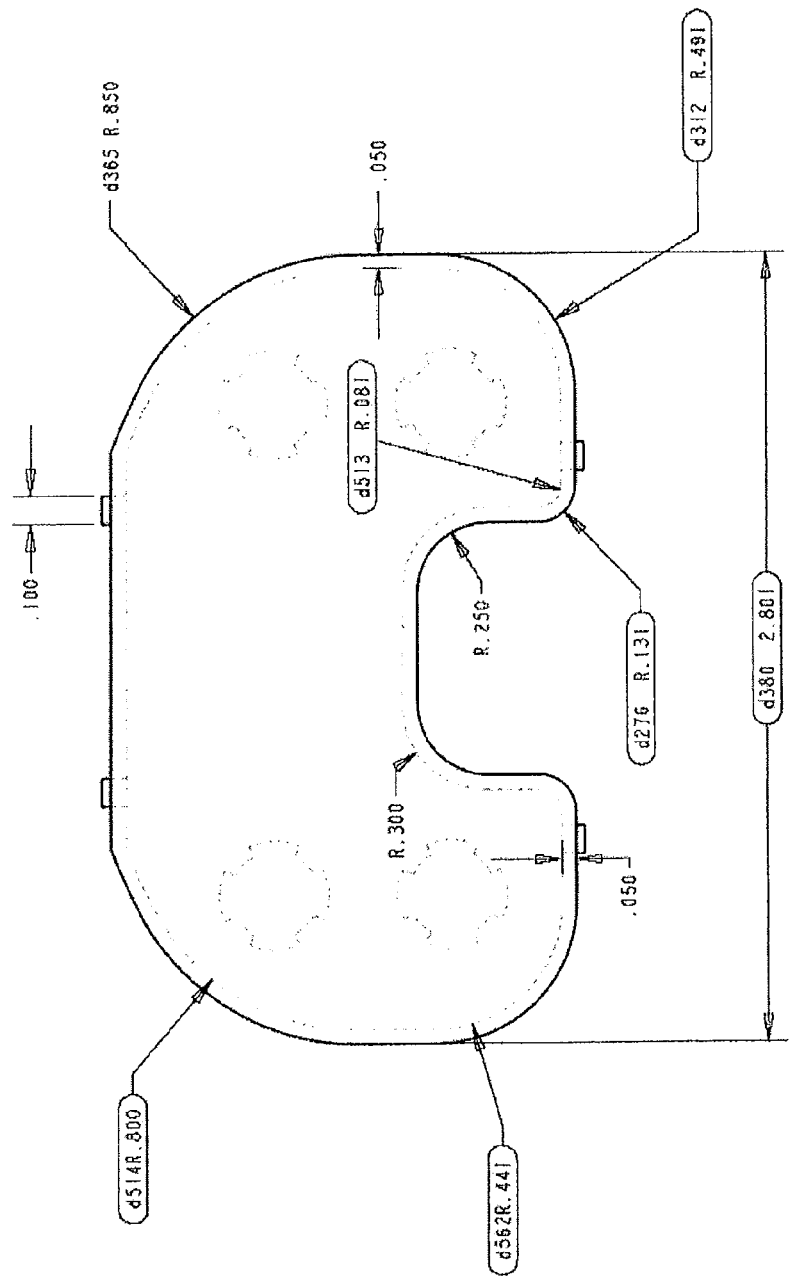
FIG. 12h is an eighth schematic of structures used in a force monitoring system.
Figure 12I:
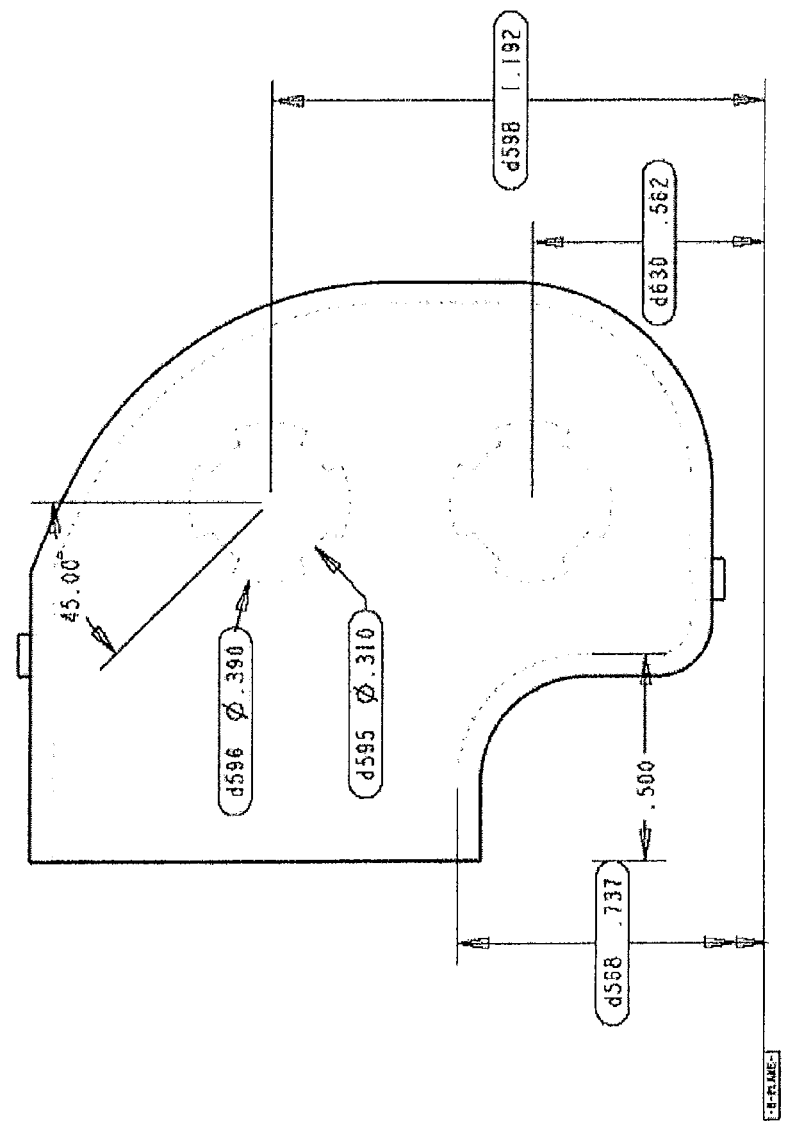
FIG. 12i is a ninth schematic of structures used in a force monitoring system.
Figure 12J:
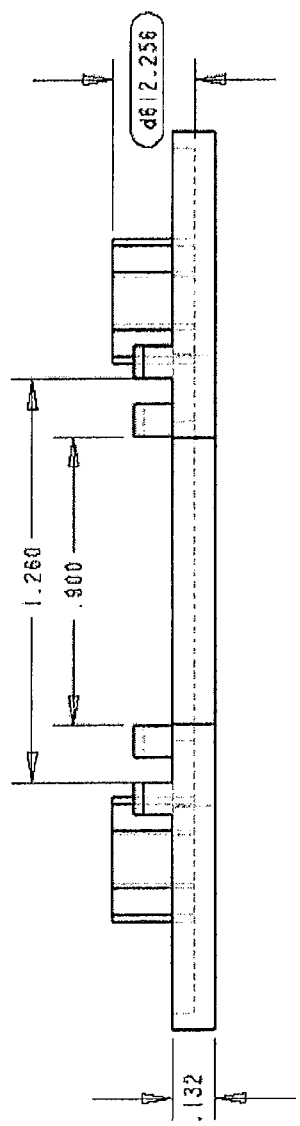
FIG. 12j is a tenth schematic of structures used in a force monitoring system.
Figure 12K:
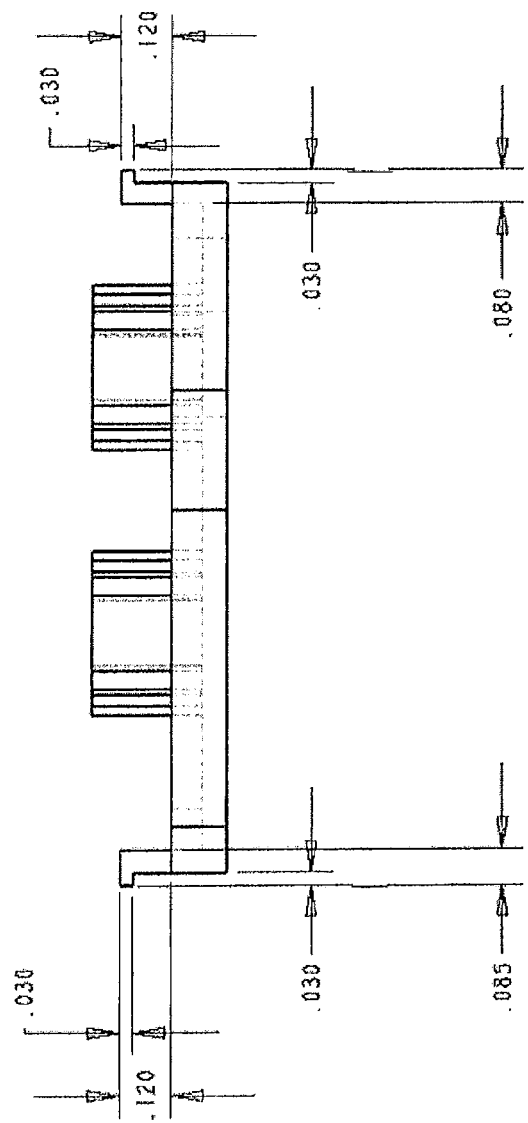
FIG. 12k is an eleventh schematic of structures used in a force monitoring system.
Figure 12I:
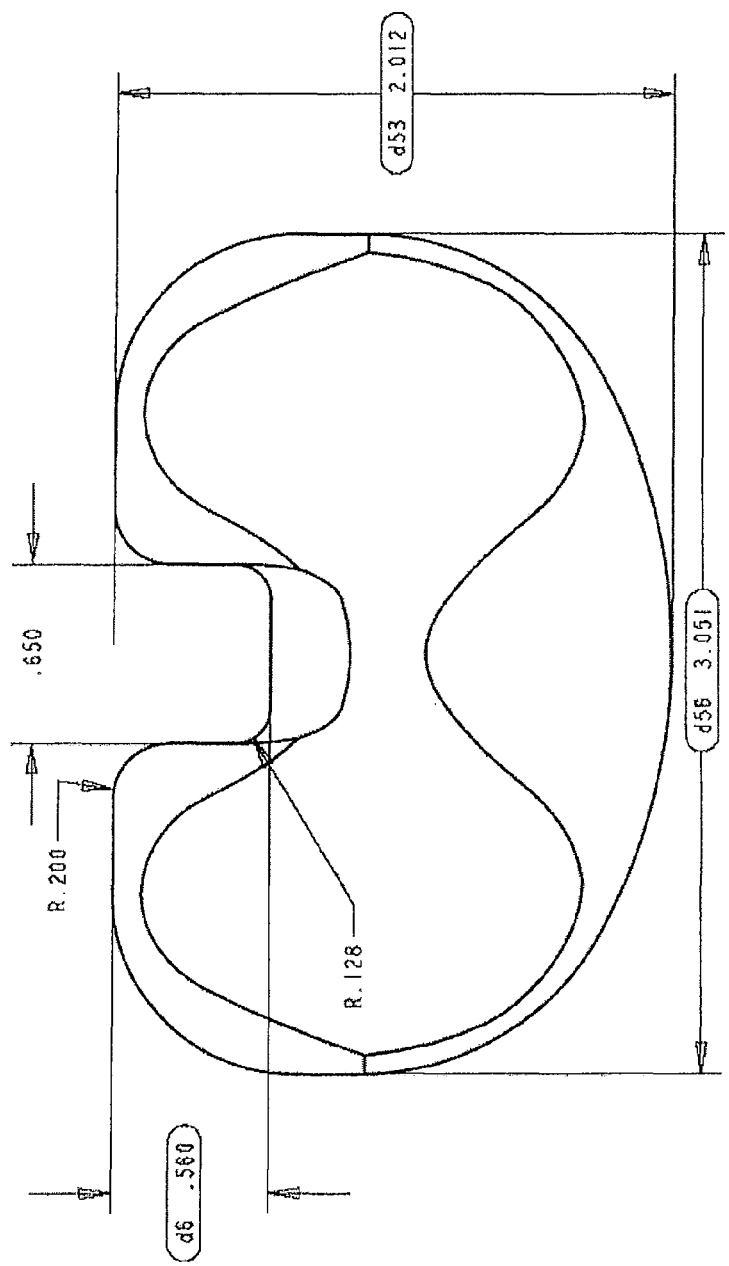
Figure 12M:
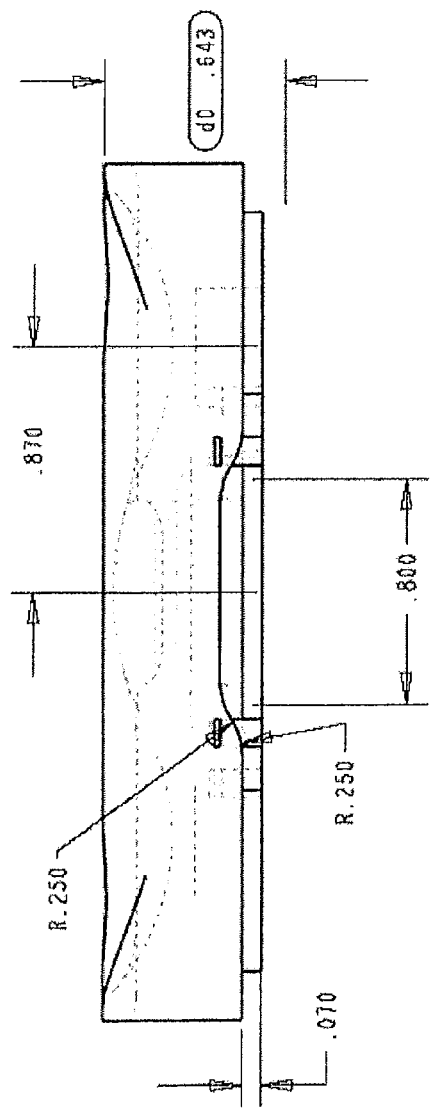
FIG. 12m is a thirteenth schematic of structures used in a force monitoring system.
Figure 12N:
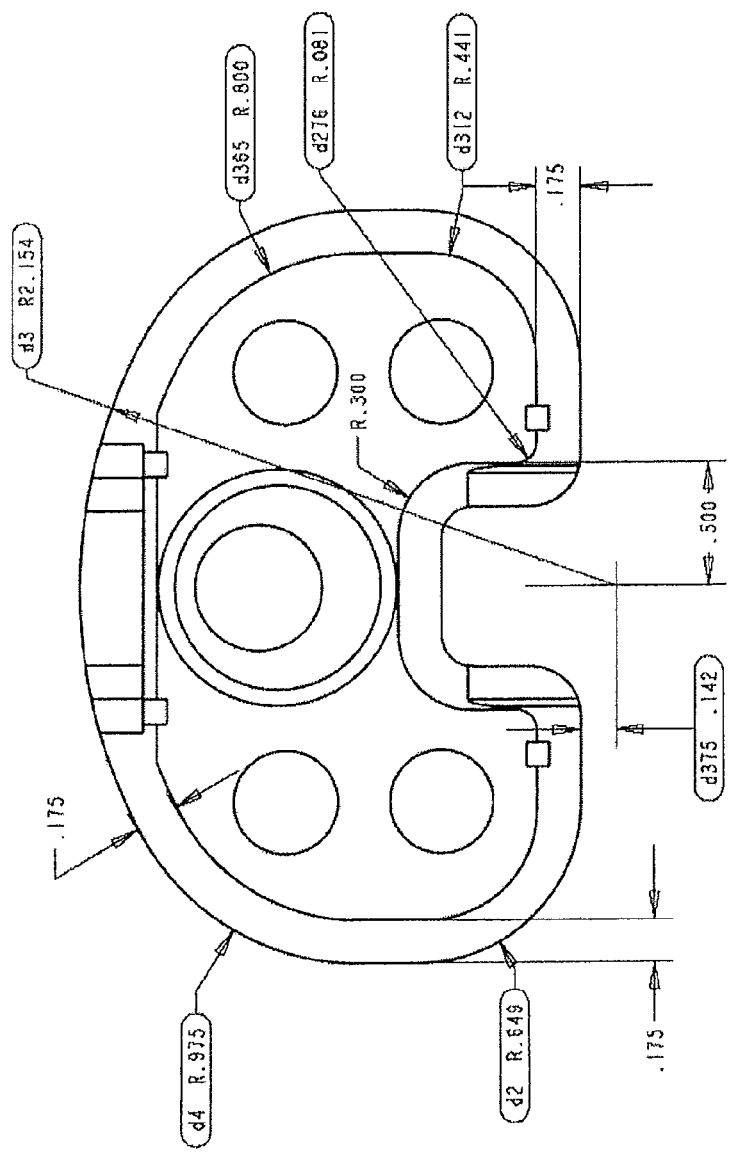
FIG. 12n is a fourteenth schematic of structures used in a force monitoring system.
Figure 12O:
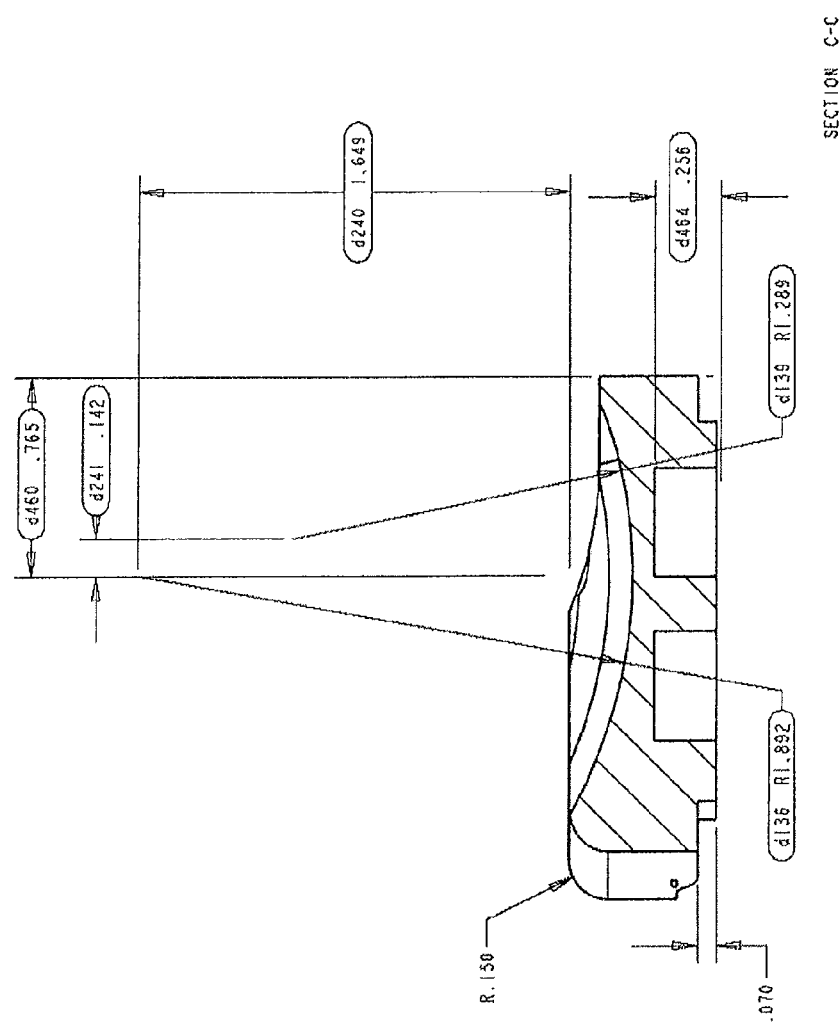
FIG. 12o is a fifteenth schematic of structures used in a force monitoring system.

In some force monitoring systems, computer 316 may comprise a MICA2DOT system that further comprises an ATMEGA128 microcontroller, a Chipcon CC1000 radio, a Panasonic ERT-J1VR103J thermistor, and Flash Memory AT45DB041 memory. The MICA2DOT system may be programmed to operate with a TINY operating system. Other force monitoring systems may use alternative shapes for poles 308, such as cylinders, hexagons, rectangles, or other polygons. The force monitoring system of the present disclosure may be manufactured according to different size specifications. In FIGS. 12a-12o, dimensions, in inches, are provided for an exemplary configuration of first body piece and second body piece for a spacer block/trial/insert (size 4 thickness 10 mm) which may be used in a TKA. Other spacer block/trial/insert sizes may range from size 1-6. For example, a spacer block/trial/insert may be categorized as a size 1.5 thickness 10 mm (e.g. SIZE__1P__5_TH10), size 3 thickness 10 mm (e.g. SIZE__3_TH10), or size 6 thickness 10 mm (e.g. SIZE__6_TH10). Additionally, size 1.5, 3, and 6, inserts may be configured with different thicknesses (measurements in mm), such as about 8, about 10, about 12.5, about 15, about 17.5, or about 20. FIGS. 13a-13d are tables providing examples of dimensions, for the structures shown in FIGS. 12a-12o, that change according to the size or thickness of the body pieces.

Figure 14:
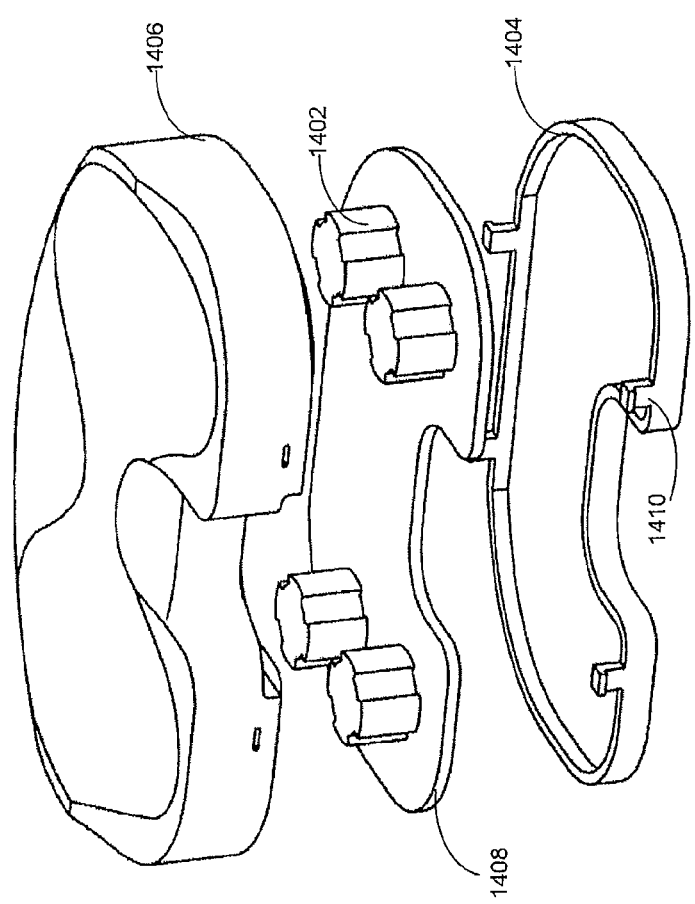
FIG. 14 is an alternative configuration for a force monitoring system.

FIG. 14 is an alternative configuration for a force monitoring system. In FIG. 14, a plurality of poles 1402 are affixed to a unitary base 1408 instead of being integrally formed in first body piece 1404. Unitary base 1408 is configured to be received in a recessed portion of first body piece 1404. Moreover, in the event that one or more of poles 1402 or one or more sensors affixed to a pole 1402 (not shown) requires maintenance, or a user wishes to add additional sensors and/or poles 1402, first body piece and second body piece 1404 and 1406 may be un-mated from one another by first disengaging snap latches 1418 and the desired maintenance or changes may then be performed.

Figure 15:
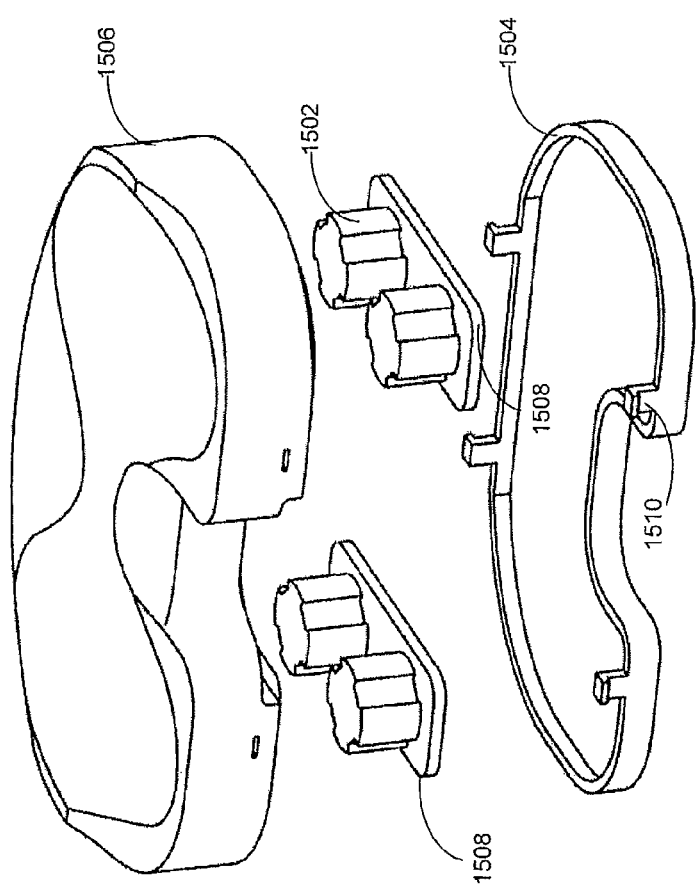
FIG. 15 is a second alternative configuration for a force monitoring system.

FIG. 15 is a second alternative configuration for a force monitoring system. In FIG. 15, a plurality of poles 1502 are affixed to a base 1508 instead of being integrally formed in first body piece 1504. Base 1508 is configured to be received in a recessed portion of first body piece 1504. Moreover, in the event that one or more of poles 1502 or one or more sensors affixed to a pole 1502 (not shown) requires maintenance, or a user wishes to add additional sensors and/or poles 1502, first body piece and second body piece 1504 and 1506 may be un-mated from one another by first disengaging snap latches 1510 and the desired maintenance or changes may then be performed. FIG. 15 differs from FIG. 14 in that changes may be performed without having to disconnect sensor connections or connections to additional hardware components (not shown) for elements whose configuration or operation is not being changed.

Figure 16:
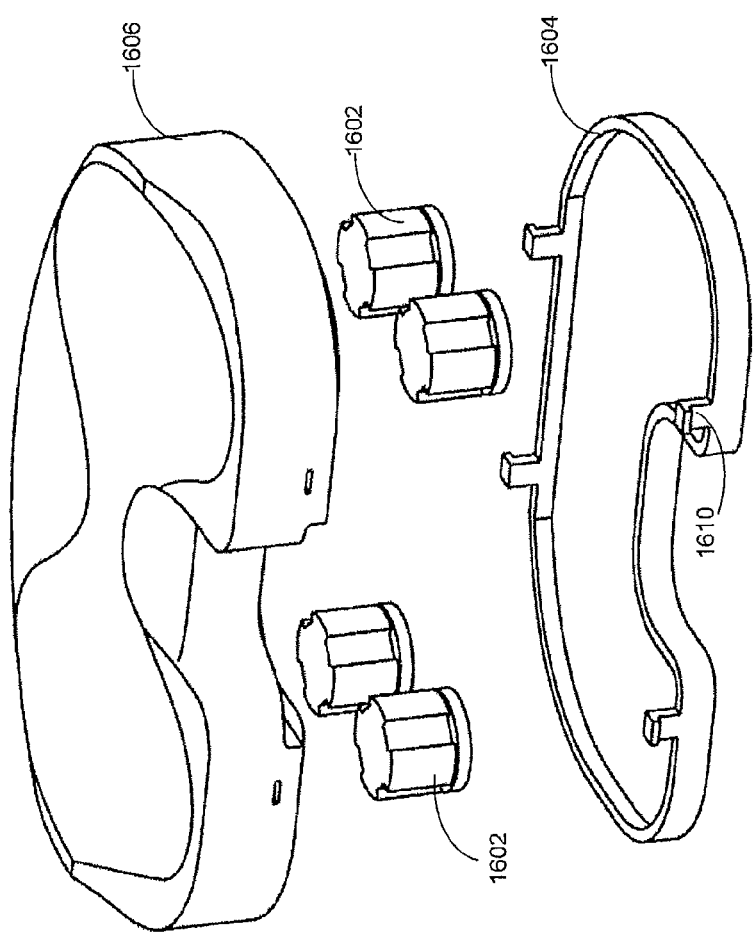
FIG. 16 is a third alternative configuration for a force monitoring system.

FIG. 16 is a third alternative configuration for a force monitoring system. In FIG. 16, a plurality of removable poles 1602 are affixed to first body piece 1604 instead of being integrally formed in first body piece 1604. In the event that one or more of poles 1602 or one or more sensors affixed to a pole 1602 (not shown) requires maintenance, or a user wishes to add additional sensors and/or poles 1602, first body piece and second body piece 1604 and 1606 may be un-mated from one another by first disengaging snap latches 1610 and the desired maintenance or changes may then be performed. FIG. 16 differs from FIG. 15 in that changes may be performed to an individual pole 1602, or additional single poles may be added without having to disconnect sensor connections or connections to additional hardware components (not shown) for elements whose configuration or operation is not being changed.

As an alternative to the force monitoring system disclosed above, some force monitoring systems may include a fully integrated structure. In these systems, the enclosure containing measurement posts and monitoring circuitry may be formed in layers, such as by injection molding. As the enclosure is being formed (molded), the monitoring circuitry may be inserted and sealed within the enclosure.

Figure 17:
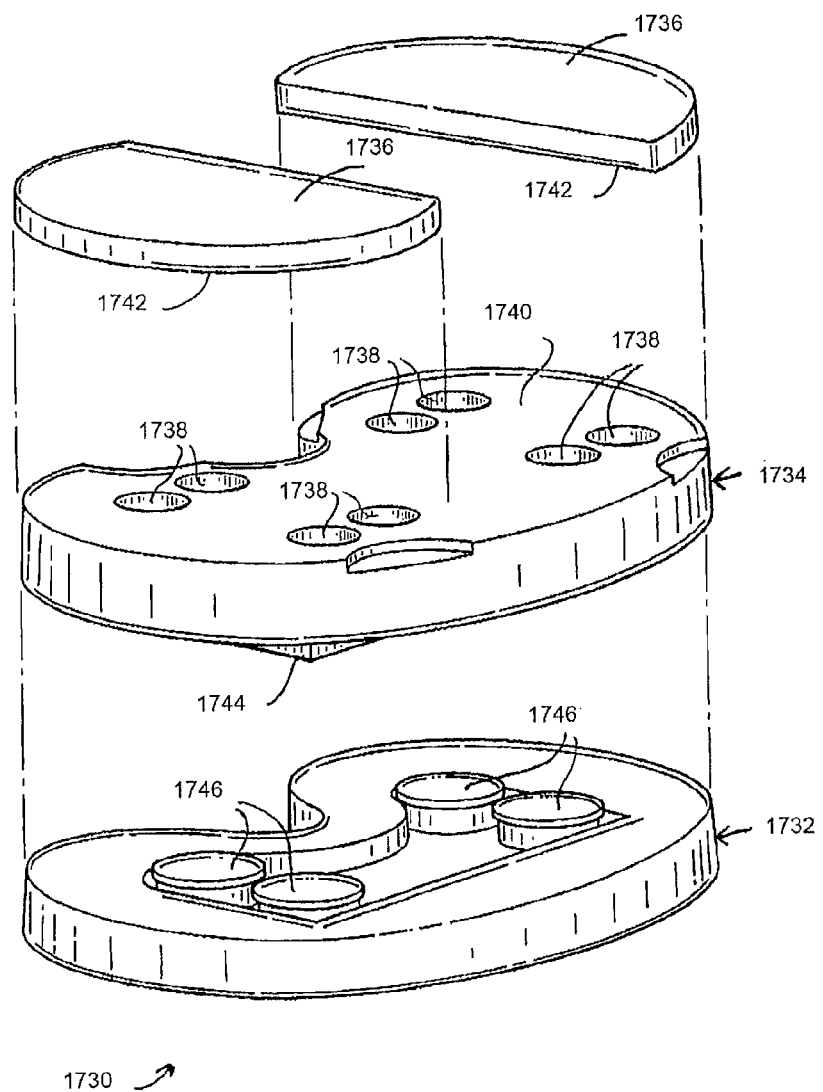
FIG. 17 is an exploded view of a spacer block of the present invention, incorporating load cells as sensors.

During a surgical procedure, and prior to the insertion of a force monitoring system enclosure (e.g., 1014) that will remain in a joint after the procedure is concluded, a spacer block may be inserted into the joint to gather data and assist the surgeon in determining whether additional bone must be removed and in selecting the appropriate trial insert or force monitoring system enclosure (e.g., 1014) that should be inserted into the joint. In some systems, the spacer block inserted into the joint may be a force monitoring system enclosure as described above. A first alternative spacer block is described with reference to FIG. 17. FIG. 17 illustrates an exemplary spacer block 1730 that may be used in conjunction with a knee joint. While illustrated with respect to a knee joint, spacer blocks may be used in conjunction with other joints.

In FIG. 17, the spacer block 1730 includes a first body piece 1732, a second body piece 1734 positioned on top of the first body piece 1732, and at least one chim 1736 positioned on top of the second body piece 1734.

As shown, in FIG. 17, two chims 1736 are mounted on top of the second body piece 1734. The chims 1736 are removably mounted onto the second body piece 1734 to allow easy replacement of the chims 1736. The chims 1736 come in various thickness, and through trial and error, chims 1736 having the proper thickness can be inserted to ensure that the data collected by the spacer block 1730 is accurate. As shown, the second body piece 1734 includes recesses 1738 formed in a top surface 1740 thereof. The chims 1736 have corresponding projections (not shown) extending from a bottom surface 1742 thereof, that engage the recesses 1738 of the second body piece 1734 to secure the chims 1736 thereon.

The first body piece 1732 includes at least one sensor to measure forces between the upper and first body pieces 1732, 1734. A processor 1744 having a memory is mounted within the second body piece 1734 and is operatively connected to the sensors when the upper and first body pieces 1732, 1734 are assembled.

As shown in FIG. 17, a plurality of load cells 1746 are positioned within the first body piece to measure compression, tension, and bending forces between the upper and first body pieces 1734, 1732. The load cells are operatively connected to the processor 1744 so information related to the forces between the upper and first body pieces 1734, 1732 can be sent to the processor. At least one load cell 1746 is associated with each chim 1736.

Shown in FIG. 17, the first body piece 1732 includes two loads cells 1746 for each chim 1736. The load cells 1746 are positioned below the chims 1736 such that the load cells 1746 will measure forces between the upper and first body pieces 1734, 1732 due to forces exerted on the chim 1736 positioned above. More loads cells 1746 will allow more data to be gathered regarding the forces on the chims 1736. Ultimately, the number of load cells 1746 used depends on the particular application.

Figure 18:
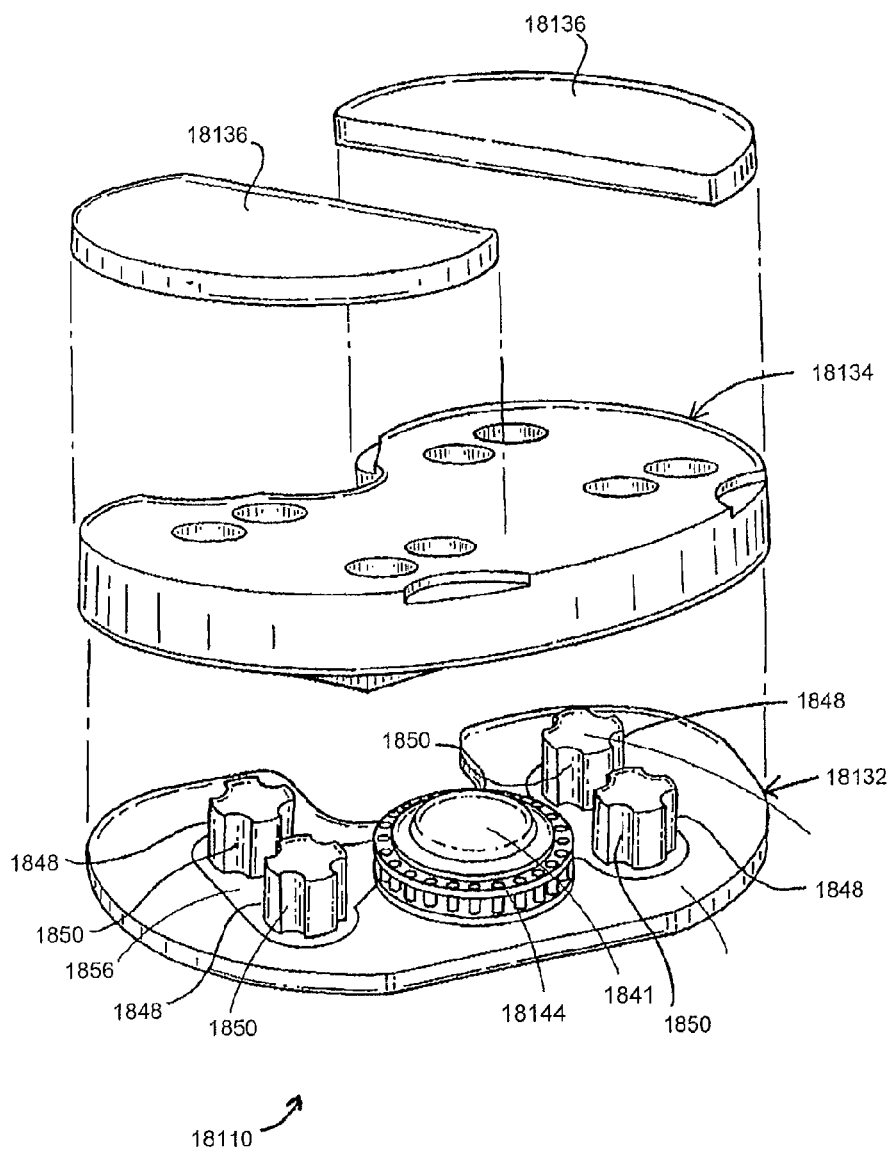
FIG. 18 is an exploded view of a spacer block of the present disclosure incorporating strain gauges as sensors.

FIG. 18 is yet another configuration of a spacer block. Spacer block 18110 includes chims 18136, a second body piece 18134, and a first body piece 18132 similar to those described above. As shown in FIG. 18, the first body piece 18132 includes a plurality of poles 1848 extending vertically upward in relation to first body piece 18132.

Figure 19:
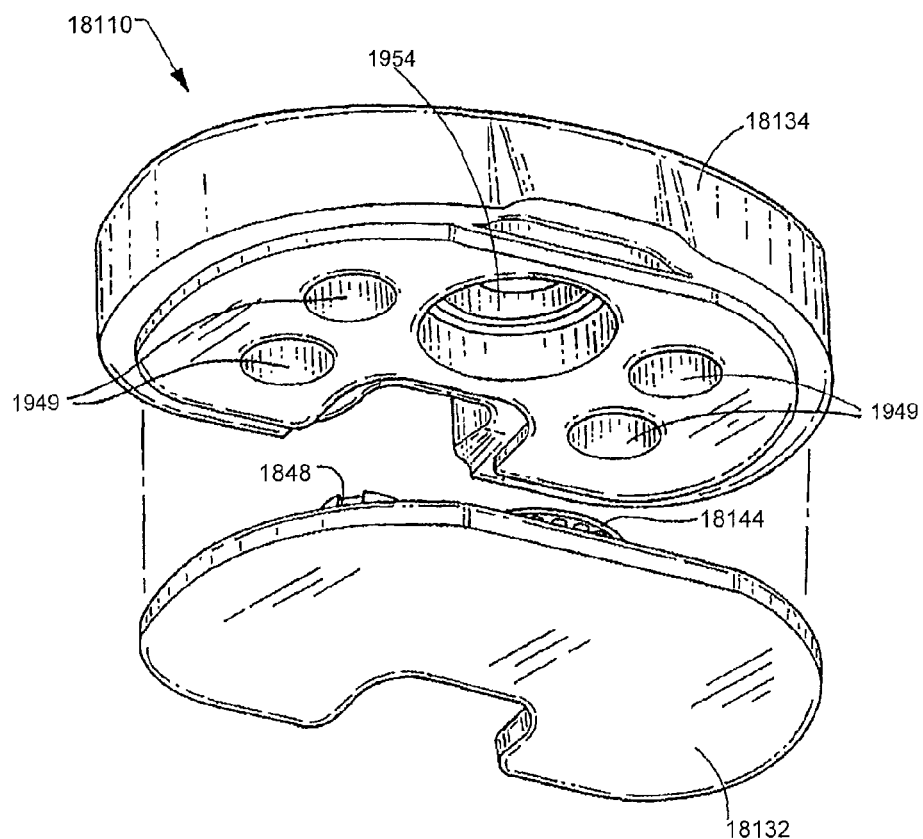
FIG. 19 is an exploded view similar to FIG. 18 from an angle showing an underside of a second body piece.

Referring to FIG. 19, the second body piece 18134 includes a plurality of pockets 1949 formed therein. The pockets 1949 are sized to accommodate the poles 1848 from the first body piece 18132. When assembled, the poles 1848 will be positioned in contact with the second body piece 18134 within the pockets 1949. There is no pre-load between the second body piece 18134 and the poles 1848, but any deflection of the second body piece 18134 will cause the second body piece 18134 to push against, and cause deflection of the poles 1848.

Figure 18A:
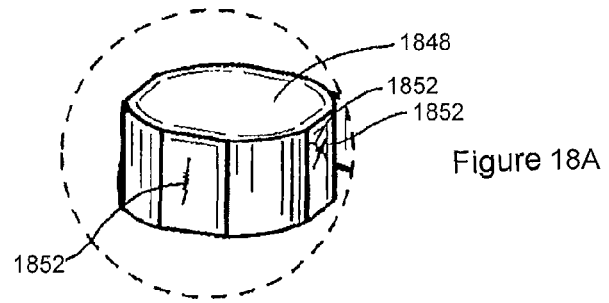
FIG. 18A is an enlarged portion of FIG. 18.

The poles 1848 have flat surfaces 1850 formed on the sides. Alternatively, grooves or slots could also be formed within the sides of the poles 1848. As shown in FIG. 18A, a plurality of strain gauges 1852 are positioned on the flat surfaces 1850 of the poles 1848 to measure compression, tension, and bending forces experienced by the poles 1848 due to contact from the second body piece 18134.

The size of the pockets 1949 formed in the second body piece 18134 is precisely calibrated to allow deflection of the poles 1848 and to ensure that when the second body piece 18134 and the first body piece 18132 are assembled, and the poles 1848 are inserted within the pockets 1949, the strain gauges 1852 are not damaged. The flat sides 1850, grooves, or slots formed on the poles 1848 provide a flat surface onto which the strain gauges 1852 can be mounted, and provide a recessed area to protect the strain gauges from damage.

The second body piece 18134 further includes a larger pocket 1954 formed to accommodate a processor 18144. The strain gauges 1852 are operatively connected to the processor 18144 via a printed circuit board or signal medium 1856 so data related to the forces on the second body piece 18134 can be sent to the processor 18144. At least one pole 1848 is associated with each chim 18136.

As shown, the first body piece 18132 includes two poles 1848 for each chim 18136. The poles 1848 are positioned below the chims 18136 such that the strain gauges 1852 will measure forces exerted on the chim 18136 positioned above. Referring to FIG. 18A, the strain gauges 1852 are positioned at different orientations to allow the strain gauges 1852 to gather force information along different directions. More strain gauges 1852 will allow more data to be gathered regarding the forces on the chims 18136. Ultimately, the number of poles 1848 and strain gauges 1852 used depends on the particular application.

A transmitter (not shown in FIGS. 17-19) may be mounted within the processor 1744, 18144. The transmitter may be adapted to take the data collected from the sensors 1746, 1852 by the processor 1744, 18144 and send the data to a remote receiver. Preferably, the receiver will analyze the data and provide feedback to help determine the proper sizing of a trial insert or force monitoring system enclosure, as more fully discussed below. Processor 1744, 18144 may be powered by battery 1841. The transmitter used in conjunction with the spacer block may be similar to the transmitter or transceiver described above in FIGS. 2-3.

In FIG. 20, a spacer block 2060 is shown having a handle 2062. The handle 2062 allows for easier manipulation and handling of the spacer block 2060. The handle 2062 of the spacer block 2060 shown in FIG. 20 is integrally formed with the spacer block 2060. The handle 2062 includes a transmitter 2064 operatively connected to the processor. The transmitter 2064 is adapted to transmit data from the processor to a remote receiver. Alternatively, the handle 2062 may include a hard wired connection 2066 to a receiver 2068 such that data from the processor can be sent to the receiver 2068, through the handle 2062, as shown in phantom in FIG. 20.

Figure 21:
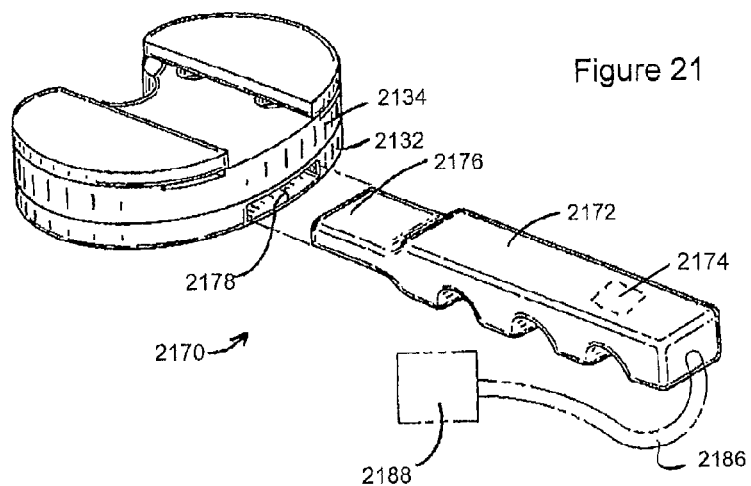
FIG. 21 is an exploded view of a spacer block having a detachable handle.

Referring to FIG. 21, a spacer block 2170 is shown having a detachably mounted handle 2172. The handle 2172 and the spacer block 2170 include features to allow an electrical connection therebetween when the handle 2172 is connected to the spacer block 2170. Any known electrical connector that is suitable for this particular application may be used. One such electrical connection is shown in FIG. 21 wherein the handle 2172 includes an insert portion 2176, and the spacer block 2170 includes a slot 2178. The insert portion 2176 and the slot 2178 have electrical connectors that are brought into contact with one another when the insert portion 2176 is inserted within the slot 2178. This type of connection is well known, and is similar to the connection of a power cable to a cell phone or the like. This type of connection could also include threaded fasteners (not shown) to allow the handle 2172 to be secured to the spacer block 2170 after the insert portion 2176 has been inserted within the slot 2178.

Figure 22:
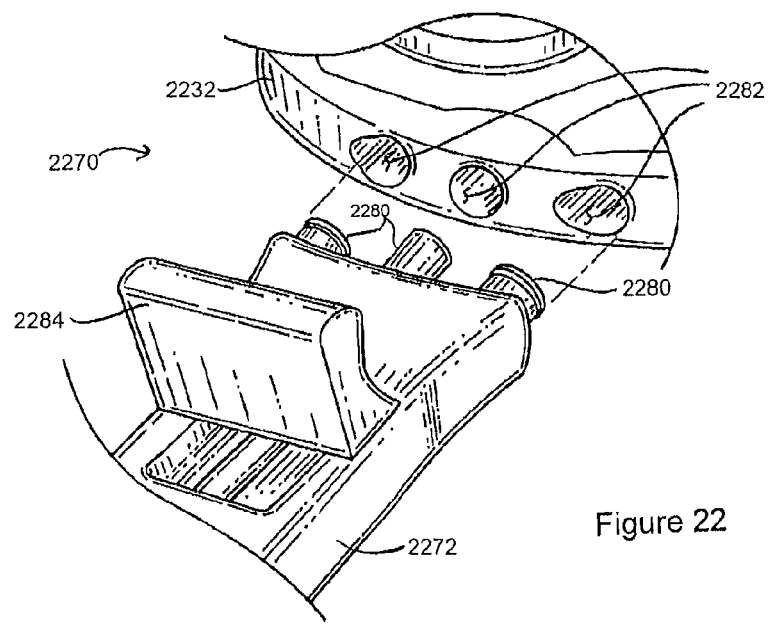
FIG. 22 is an exploded view of a portion of a spacer block having detachable handle of another embodiment.

An alternate type of electrical connection is shown in FIG. 22, wherein the handle 2272 includes projecting conductors 2280 and the spacer block 2232 includes openings 2282 to receive the conductors 2280. The conductors 2280 may be asymmetrical and rotatable, such that after insertion into corresponding shaped openings 2282, the conductors 2280 may be rotated by actuating a lever 2284, thereby locking the handle 2272 to the spacer block 2270.

As described above, the detachable handle 2272 may also include a transmitter 2174 that is operatively connected to the processor through the electrical connection between the handle 2172 and the spacer block 2170. The transmitter 2174 is adapted to transmit data from the processor to a remote receiver, when the handle 2172 is connected to the spacer block 2170. Alternatively, the handle 2272 may include a hard wired connection 2186 to a receiver 2188 such that data from the processor can be sent to the receiver 2188, through the handle 2172, when the handle 2172 is connected to the spacer block 2170, as shown in phantom in FIG. 21.

Figure 23:
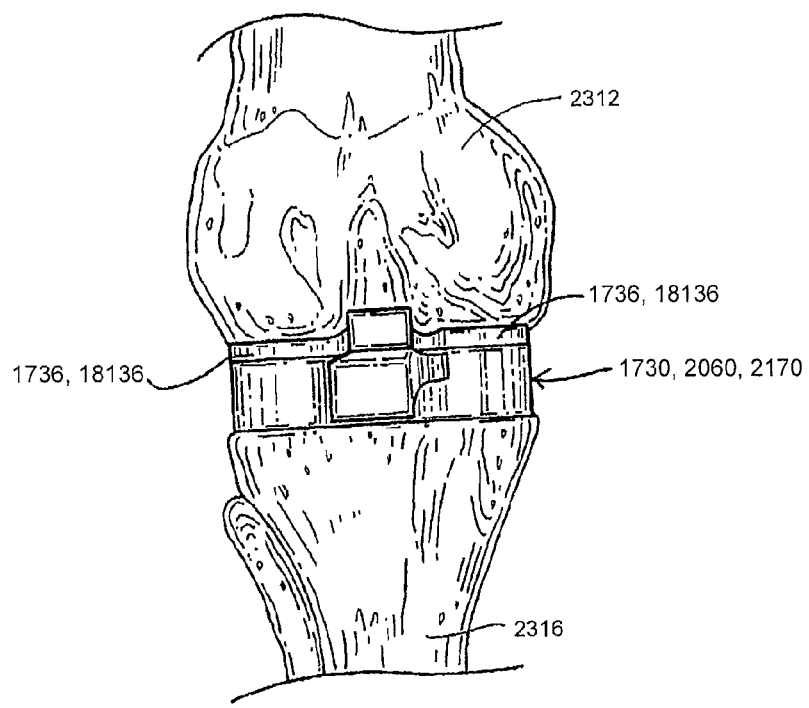
FIG. 23 is a plan view of a human knee having a spacer block of the present disclosure placed between a femur and a tibia.

In FIG. 23, the spacer block 1730, 2060, 2170 is fully shown assembled and disposed in a joint. In FIG. 23, the exemplary joint is a knee joint. As shown in FIG. 23, the spacer block 1730, 2060, 2170 is positioned between the femur 2312 and the tibia 2316, the sensors (strain gauges 1852, or load cells 1746) are responsive to the forces imposed by the femur 2312 upon the chims 1736, 18136. Furthermore, the sensors may provide data in a real-time, or near real-time fashion, allowing for intraoperative analysis of the data. Specifically, the processor 1844, 18144 contains a memory for storing the data. In operation, the processor 1844, 18144 is adapted to receive, as an input, multiple sensor outputs created by each of the strain gages 1852 or load cells 1746 in response to forces exerted on the chims 1736, 18136. The processor 1844, 18144 may be coupled to a transmitter 2064, 2174 that is adapted to convert the multiple sensor inputs to a data stream, such as a serial data stream, and transmit the data stream, via wired or wireless connection, to a receiver 2068, 2188 as described above.

Figure 24:
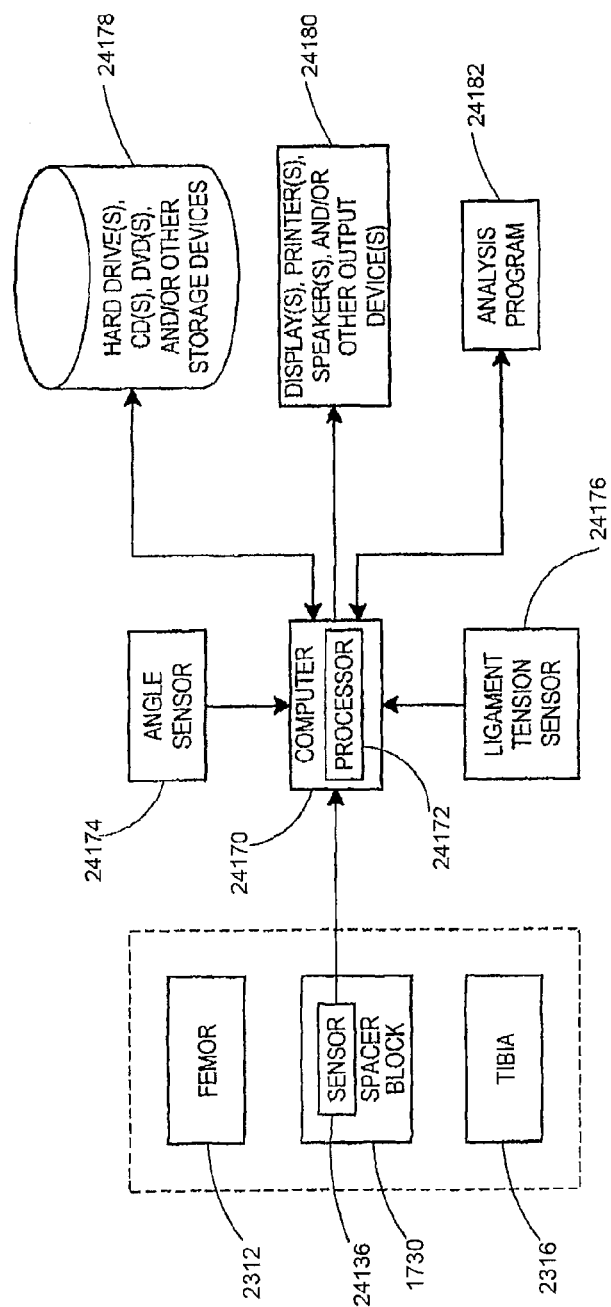
FIG. 24 is a block diagram depicting various components of a joint prosthesis fitting and balancing system.

As shown in FIG. 24, a computer 24170 having processor 24172 and a memory coupled thereto is in communication with at least one sensor 24136, which is embedded within the spacer block 1730. If desired, the computer 24170 may communicate with ancillary components 24178, 24180, and 24182, as described in greater detail in applicant's related U.S. Patent Application Pub. No. 2004/0019382 A1. For example, in one embodiment the output device 24180 may display output plots, images, or other data in terms of a force and position of the force imposed upon a joint. Further, if desired, optional joint angle sensor 24174 and optional ligament tension sensor 24176 may be used during the joint replacement procedure to acquire additional data, as generally described in applicant's above-referenced application.

While various embodiments of the invention have been described, it will be apparent to those of ordinary skill in the art that many more embodiments and implementations are possible within the scope of the invention. Accordingly, the invention is not to be restricted except in light of the attached claims and their equivalents.

I claim:

1. A system that gathers information to select a trial insert between a femur and tibia of a knee of a patient, comprising:
    a first body piece and a second body piece of a spacer, the first body piece being separate from the second body piece, where the first body piece and the second body piece can be assembled together to form the spacer, the first body piece comprising a plurality of poles integrally formed with the first body piece and extending relative to an inside surface of the first body piece;
    a plurality of sensors disposed on each respective pole;
    a processor positioned between the first body piece and the second body piece when the first and the second body pieces are assembled, the processor coupled with the plurality of sensors; and
    a chim removably mountable to an outside surface of the second body piece, the plurality of poles disposed about and aligned with the chim, and where the chim is configured to be mountable to the outside surface of the second body piece through projections on an underside of the chim and corresponding recesses formed in the top surface of the second body piece that align with the plurality of poles.

2. The system of claim 1, where the second body piece comprises a plurality of apertures configured to receive the plurality of poles.

3. The system of claim 1, where the plurality of sensors are configured to detect a mechanical motion of a respective pole based on a force exerted on the chim, and where the processor is configured to receive a signal from the sensors and provide a measurement of a magnitude of compression experienced by the plurality of poles.

4. The system of claim 3, further comprising a transmitter disposed between the between the first body piece and the second body piece when they are assembled together, and where the processor is configured to transmit the measurement of the magnitude of compression to a remote computer through the transmitter.

5. The system of claim 1, where the plurality of sensors are configured to detect a mechanical motion of a respective pole based on a force exerted on the chim, and where the processor is configured to receive a signal from the sensors and provide a measurement of a magnitude of tension experienced by the plurality of poles.

6. The system of claim 5, further comprising a transmitter disposed between the between the first body piece and the second body piece when they are assembled together, and where the processor is configured to transmit the measurement of the magnitude of tension to a remote computer through the transmitter.

7. The system of claim 1, where the plurality of sensors are configured to detect a mechanical motion of a respective pole based on a force exerted on the chim, and where the processor is configured to receive a signal from the sensors and provide a measurement of a magnitude of bending force experienced by the plurality of poles.

8. The system of claim 7, further comprising a transmitter disposed between the between the first body piece and the second body piece when they are assembled together, and where the processor is configured to transmit the measurement of the magnitude of bending force to a remote computer through the transmitter.

9. The system of claim 1, further comprising a handle mounted to the spacer.

10. The system of claim 9, where the handle is detachably connected to the spacer.

11. The system of claim 9, where the plurality of sensors are configured to detect a mechanical motion of a respective pole based on a force exerted on the chim, and where the processor is configured to receive a signal from the sensors and provide a measurement of the mechanical motion.

12. The system of claim 9, further comprising a transmitter disposed in the handle and coupled to the processor, and where the processor is configured to transmit the measurement of the mechanical motion to a remote computer through the transmitter.

13. The system of claim 1, where each of the plurality of poles comprise a recessed wall.

14. The system of claim 13, where a top portion of a pole conforms to a shape of a condyle.

15. The system of claim 13, where a sensor is disposed in the recessed wall of one of the plurality of poles.

16. The system of claim 1, where the plurality of sensors are configured to detected a mechanical motion of the spacer.

17. A system to plurality of poles integrally that gathers information to select a trial insert between a femur and tibia of a knee of a patient, comprising:
    a first body piece and a second body piece of a spacer, the first body piece being separate from the second body piece, where the first body piece and the second body piece can be assembled together to form the spacer, the first body piece comprising a plurality of poles integrally formed with the first body piece and extending relative to an inside surface of the first body piece, where a top portion of at least one of the plurality of poles conforms to a shape of a condyle to mate with an underside portion of the second body piece;

a plurality of sensors disposed on each respective pole;

a processor positioned between the first body piece and the second body piece when the first and the second body pieces are assembled, the processor coupled with the plurality of sensors; and a chim removably mountable to an outside surface of the second body piece, the plurality of poles disposed about and aligned with the chim, and where the chim is configured to be mountable to the outside surface of the second body piece through projections on an underside of the chim and corresponding recesses formed in the top surface of the second body piece.

18. A system that gathers information to select a trial insert between a femur and tibia of a knee of a patient, comprising:

a first body piece and a second body piece of a spacer, the first body piece being separate from the second body piece, where the first body piece and the second body piece can be assembled together to form the spacer, the first body piece comprising a plurality of poles integrally formed with the first body piece and extending relative to an inside surface of the first body piece;

a plurality of sensors disposed on each respective pole;

a processor positioned between the first body piece and the second body piece when the first and second body pieces are assembled, the processor coupled with the plurality of sensors; and at least two separate chims removably mountable to an outside surface of the second body piece, where each of the separate chims is associated with a pole from the plurality of poles, and wherein each separate chim is configured to be mountable to an outside surface of the second body piece through projections on an underside of the chim and associated recesses formed in the top surface of the second body piece corresponding with the associated pole.

* * * * *